(12) United States Patent
Wilson

(10) Patent No.: US 7,575,890 B2
(45) Date of Patent: Aug. 18, 2009

(54) METHOD FOR RAPID DETECTION AND EVALUATION OF CULTURED CELL GROWTH

(75) Inventor: David F. Wilson, Philadelphia, PA (US)

(73) Assignee: Oxygen Enterprises, Ltd., Philadelphia, PA (US)

( * ) Notice: Subject to any disclaimer, the term of this patent is extended or adjusted under 35 U.S.C. 154(b) by 0 days.

(21) Appl. No.: 11/334,236

(22) Filed: Jan. 18, 2006

(65) Prior Publication Data

US 2007/0166780 A1 Jul. 19, 2007

(51) Int. Cl.
*C12Q 1/04* (2006.01)
*C12N 5/02* (2006.01)
*G01N 21/76* (2006.01)
*C07D 497/22* (2006.01)
*C07D 47/04* (2006.01)
*C07D 205/00* (2006.01)

(52) U.S. Cl. .................. 435/34; 435/382; 436/172; 540/124; 540/140; 540/201

(58) Field of Classification Search .................. None
See application file for complete search history.

(56) References Cited

U.S. PATENT DOCUMENTS

| | | | |
|---|---|---|---|
| 4,411,997 A | 10/1983 | Shimazaki et al. | 435/115 |
| 4,568,737 A | 2/1986 | Tomalia et al. | 528/332 |
| 4,947,850 A | 8/1990 | Vanderkooi et al. | 128/654 |
| 5,041,516 A | 8/1991 | Fréchet et al. | 528/44 |
| 5,098,475 A | 3/1992 | Winnik et al. | 106/22 |
| 5,256,193 A | 10/1993 | Winnik et al. | 106/21 |
| 5,279,297 A | 1/1994 | Wilson et al. | 128/633 |
| 5,393,795 A | 2/1995 | Hedstrand et al. | 521/134 |
| 5,393,797 A | 2/1995 | Hedstrand et al. | 521/134 |
| 5,418,301 A | 5/1995 | Hult et al. | 525/437 |
| 5,523,214 A | 6/1996 | Horn | 435/52 |
| 5,837,865 A | 11/1998 | Vinogradov et al. | 540/145 |
| 6,165,741 A | 12/2000 | Wilson et al. | 435/34 |
| 6,274,086 B1 | 8/2001 | Wilson et al. | 422/82.08 |
| 6,362,175 B1 | 3/2002 | Vinogradov et al. | 514/185 |
| 6,701,168 B1 | 3/2004 | Wilson et al. | 600/317 |
| 6,777,226 B2 | 8/2004 | Jeffrey et al. | 435/287.7 |

OTHER PUBLICATIONS

Omar, S.H. Oxygen Diffusion Through Gels Employed for Immobilization 1. in the Absence of Microorganisms; Applied Microbiology and Biotechnology, vol. 40 (1993) pp. 1-6.*
Dunphy et al., "Oxyphor R2 and G2: phospors for measuring oxygen by oxygen-dependent quenching of phosphorescence", Anal. Biochem. (2002) 310:191-198.
Hooijmans et al., "Measurement of oxygen concentration gradients in gel-immobilized recombinant *Escherichia coli* ", Appl. Microbiol. Biotechnol. (1990) 33:611-618.
Lähdesmäki et al., "Novel flow injection methods for drug-receptor interaction studies, based on probing cell metabolism", Analyst (1989) 125:1889-1895.

Vinogradov and Wilson, "Metallotetrabensoporphyrins. New Phosphorescent Probes for Oxygen Measurements", J. Chem. Soc., Perkin Trans. (1995) 2:103-111.
Eagle, "Nutrition Needs of Mammalian Cells in Tissue Culture", *Science* 122:501-504 (1955).
Eagle, "Amino Acid Metabolism in Mammalian Cell Cultures", *Science* 130:432-437 (1959).
Griethuysen, et al., *J. Clin. Microbiology* 34 (10), pp. 2391-2394 (Oct. 1996).
Ince, et al., Microcirculatory Oxygenation and Shunting in Sepsis and Shock, *Critical Care Med.*, vol. 27, No. 7, pp. 1369-1377 (Jul. 1999).
Jin et al, *J. Chem Soc. Chem. Commun.* 16, pp. 1260-1262, (Aug. 1993).
Lo, et al., "Calibration of Oxygen-Dependent Quenching of the Phorphorescence of Pd-meso-tetra (4-Carboxyphenyl) Porphyrine: A Phosphor with General Application for Measuring Oxygen Concentration in Biological Systesm," *Analy. Biochem.* 236:153-160 (1996).
Motterlini, et al., Depression of Endothelial and Smooth Muscle Cell Oxygen Consumption by Endotoxin; *American Journal of Physiology*, vol. 275, No. 168, p. 776-782, (Sep. 1998).
Pawlowski, M., et al., "Monitoring of the Oxygen Pressure in the Blood of Live Animals Using the Oxygen Dependent Quenching of Phosphorescense", *Adv. Exp. Med. Biol.* 316:179-185 (1992).
Robiolio, et al."Oxygen Diffusion and Mitochondrial Respiration in Neuroblastoma Cells," *AM. J. Physiol.* 256(6 Pt. 1):C1207-1213 (Jun. 1989).
Shrager, "Quadratic Programming for Nonlinear Regression," *Numerical Mathematics*, 15:41 (1972).
Vinogradov et al., "*Metallotetrabenzoporphyrins. New Phosphorescent Probes for Oxygen Measurements,*" *Chem. Soc. Trans.* 2, pp. 103-109 (1995).
Vanderkooi, et al., "An Optical Method for Measurement of Dioxygen Concentration Based upon Quenching of Phosphorescence", *J. Biol. Chem.* 262, No. 12:5476-5482 (Apr. 1987).

(Continued)

Primary Examiner—Jon P Weber
Assistant Examiner—Paul C. Martin
(74) Attorney, Agent, or Firm—Evelyn H. McConathy; Montgomery, McCracken, Walker & Rhoads, LLP

(57) ABSTRACT

Provided is a method and system for the rapid and accurate detection of growth and metabolism of a cellular microorganism in a population of microorganisms in a non-liquid, culture medium. Further provided is a gelled culture medium containing a non-toxic, water-soluble, phosphorescent compound which measures oxygen content (partial pressure) of an microorganism also contained therein, by oxygen-dependent quenching of phosphorescence; or the gel contains a fluorescent pH indicator that demonstrates growth of the microorganism by pH-dependent intensity change or wavelength shift in the emission spectrum. Further provided is a system and method for killing undesirable microorganisms or colonies in the culture medium without harming the surrounding microorganisms.

12 Claims, 5 Drawing Sheets

OTHER PUBLICATIONS

Wilson, et al., "The Oxygen Dependence of Mitochondrial Oxidative Phosphorylation Measured by a New Optical Method for Measuring Oxygen Concentration", *J. Biol. Chem.*, 263:2712-2718 (1988).

Wilson, et al., "Effect of Hyperventilation on Oxygenation of the Brain Cortex of Neonates," *Adv. Exp. Med. Biol.*, 316:341-346 (1992).

* cited by examiner

METHOD FOR RAPID DETECTION AND EVALUATION OF CULTURED CELL GROWTH

FIELD OF THE INVENTION

The present invention provides a method for rapidly detecting and monitoring growth of microorganisms immobilized within a gelled culture material using oxygen-quenchable phosphorescent compounds or fluorescent pH indicators.

BACKGROUND OF THE INVENTION

Growth characteristics vary widely from one microorganism to another. For example, it has been estimated that relatively-rapidly growing *Mycobacteria* require approximately one week to demonstrate growth, whereas relatively more slowly-growing tuberculosis agents, such as *M. tuberculosis, M. bovis* and *M. avium*, which are also known to appear in AIDS patients, require at least eight to ten weeks of incubation under conventional conditions before growth is detectable by standard methods. As a result, methods for the rapid detection and accurate measurement of the cell growth of various microorganisms are useful for a variety of purposes, including monitoring yields in the production of microorganisms in industrial fermentation processes and the early detection of pathogenic microorganisms.

Growing microorganisms in liquid culture is a well-known technique. See, for instance, Sambrook et al. (1989, Molecular Cloning: A Laboratory Manual, Cold Spring Harbor Laboratory, New York); Ausubel et al. (1997, Current Protocols in Molecular Biology, John Wiley & Sons, New York); and Gerhardt et al. (eds., 1994, Methods for General and Molecular Bacteriology, American Society for Microbiology, Washington, D.C.). When microorganisms are grown in a liquid culture medium, an accurate measure of the rate of oxygen depletion in the liquid culture medium can be used to determine, the presence of viable organisms in the culture following inoculation, as well as the rate of growth of that organism in the culture (see, e.g., U.S. Pat. No. 6,165,741).

Growth in liquid culture, however, is less useful for rapid identification of a slow-growing microorganism, particularly if there is a mixture of microorganisms and one seeks to identify individual clonal colonies. The longer a microorganism is cultured, the greater the risk of contamination, usually by a fast-growing bacteria, yeast or fungus. Fast-growing microorganisms tend to out-compete slow-growing microorganisms and overgrow the culture, obscuring the slow-growing microorganisms. Furthermore, in such a mixture of microorganisms, one can no longer identify and select individual cells for isolated growth.

Plating microorganisms onto a layer of agar or other growth media has long been used to separate individual microorganisms and permit isolating clonal growth of individual cells. Such techniques are well known to the skilled artisan. See, for instance, Sambrook et al., supra, 1989; Ausubel et al., supra, 1997; Gerhardt et al., supra, 1994). Plating slow-growing microorganisms, however, still requires long incubation periods to detect growth by conventional means, increasing the risk of contamination over time and increased handling.

Several methods are known for the detection of cell growth, such as U.S. Pat. No. 5,523,214, which describes a method for visually demonstrating the cell growth in broths or gels of microorganisms. Microorganisms include, for example, fungi, yeasts and bacteria, including *Mycobacteria*, non-fermenters, *cocci, bacilli, coccobacilli, enterobacteria* and the like, obtained from urine specimens, matter from wounds and abscesses, blood, sputum, etc. However, the detection method of the '214 patent utilize a redox indicator in the medium, meaning that the method is not commercially practical because the amount of redox indicator that is required to demonstrate growth of the microorganism may also be toxic to the cells, and/or such methods require an inordinate amount of care to avoid toxicity and prevent false negative results. Furthermore, like all other prior art methods, when the '214 method is used to detect the growth of slow-growing cells in culture, the cells require several weeks in culture before microbial cell growth is demonstrated. To date, with the exception of the inventor's own work, none of the available detection methods provide rapid and reliable detection of cell growth in culture in a matter of only a day or two.

Based upon the principle that oxygen quenches phosphorescence in an aqueous liquid growth medium, U.S. Pat. No. 6,165,741 provides one method for detecting growth or metabolism of microorganisms in culture. In a liquid culture medium containing a dissolved oxygen-quenchable phosphorescent compound, as the microbial sample grows, oxygen is consumed, and the oxygen quenching of the phosphorescent compound decreases. In other words, phosphorescence, indicative of growth or metabolism of the microorganisms, increases in direct ratio with cell growth and is quantitatively detectable at measurable levels in the culture medium. However, the typical volume of liquid culture media used to grow the cells in standard plates or vessels in the '741 patent requires the use of substantial volumes of reagent and marker materials, and while more rapid than other methods, several days are needed to provide reliable readings using this method. Moreover, because liquid culture techniques are used, the '741 patent does not permit the rapid identification and isolation of individual clonal colonies.

Hooijmans et al. ((1990) *Appl. Microbiol. Biotechnol.* 33:611-618) teach measurement of time-dependent oxygen concentration gradients of *E. coli* immobilized in gel beads or a cylindrical tube gel. Oxygen is measured using an oxygen microsensor comprising a flow chamber, a micromanipulator and a stereomicroscope, then the measured data is captured by a computer. However, the complexity of this method and the requirement of using specialized equipment, including an oxygen microsensor, makes it unsuitable for rapid growth detection purposes.

Lähdesmädki et al. ((1989) *Analyst* 125:1889-1895) disclose immobilizing cells in an agarose matrix, which is sandwiched between a physical support and the surface of an electrochemical pH sensor (Cytosensor Microphysiometer). A fluorescent technique is used to monitor change in pH of the growing microorganisms. In addition, the investigator discloses the use of disposable samples of cells grown on microcarrier beads labeled with a fluorescent pH indicator for use with the electrochemical pH sensor. However, this method suffers from the same drawbacks as the other prior art methods. Although a fluorescent indicator is used, because the cells are not immobilized, the disclosed methods cannot provide a means for isolating an individual cell or colony from the culture media.

Jeffrey et al. (U.S. Pat. No. 6,777,226) disclose a sensor device for detecting microorganisms. The sensor device discloses a multilayer construct, having a matrix layer to immobilize the microorganisms, and a sensor layer comprising a fluorescent indicator, which is used to monitor growth of the microorganisms. However, in the '226 patent, the sensor layer is a separate entity from the immobilization matrix layer.

Thus, until the present invention there has remained an unmet need in the art for a method of monitoring and rapidly detecting cell growth using a simple system that does not require complex microsensors, layering or risk of toxicity to the cells that could produce false negatives, while at the same time allowing for the collection of the individual colonies for further growth, manipulation and evaluation. Preferably, such detection methods would produce reliable results in a day or less, and would permit rapid and sensitive detection of cell growth down to statistical limits in terms of number of organisms per sample. Furthermore, such a method should be optimally adapted to an automated format.

SUMMARY OF THE INVENTION

The present invention provides a method for rapidly detecting growth or metabolism of an immobilized cellular microorganism, comprising immobilizing a population of cells of at least one microorganism in an aqueous gelling medium comprising a dissolved oxygen-quenchable phosphorescent compound that is non-toxic to the microorganism; thereby maintaining communicable contact between each cell and the oxygen-sensitive phosphor in the surrounding medium, such that the phosphorescent compound is responsive to oxygen pressure in the medium; exciting the dissolved phosphorescent compound to phosphoresce; and detecting the phosphorescence in the gelling medium, wherein an increase in phosphorescence is indicative of growth or metabolism of the microorganism. The non-toxic, soluble, oxygen-quenchable phosphorescent compound is preferably a porphyrin compound, more preferably a first, second, third, fourth or fifth generation dendrimer, as disclosed in greater detail below.

Also provided is a method detecting growth or metabolism of an immobilized anaerobic microorganism, comprising immobilizing a population of cells of at least one anaerobic microorganism in an aqueous gelling medium comprising a dissolved fluorescent pH indicator compound that is non-toxic to the microorganism; thereby maintaining communicable contact between each cell and the fluorescent pH indicator in the surrounding medium, such that the fluorescent pH indicator is responsive to hydrogen ion changes in the medium; exciting the dissolved fluorescent indicator to fluoresce, and detecting a change in fluorescence emission by the fluorescent pH indicator in the gelled culture medium, wherein a change in fluorescence emission is indicative of a hydrogen ion change resulting from growth or metabolism of the microorganism. Thus, the needs described above are met, as are others, as will be further described below.

In addition, the present invention provides a hollow-form growth chamber for use in rapidly detecting growth or metabolism of a microorganism, which may be preformed or premolded, or which may be formed as needed, and which may further comprise a sterile, disposable, puncture-resistant plastic culture bag. In the alternative, the culture bag may replace the hollow-form chamber.

Further provided is a system for killing one or more undesirable microorganism(s) immobilized in a gel within a growth chamber, wherein the system comprises: an excitation light source, a light detector, a collimated laser diode, a means for positioning a growth chamber device relative to said collimated laser diode, and a processing means operably interconnecting the excitation light source, the light detector and the collimated laser diode. In one embodiment of the invention, the excitation light source excites a photoluminescent molecule within the growth chamber, then the light detector detects light emitted from the photoluminescent molecule, and the processing means aims the collimated laser diode in response to the detected light emission and activates the laser diode to an intensity sufficient to kill one or more selected undesirable microorganism(s) immobilized within the growth chamber without killing desirable surrounding microorganisms. Also provided is a method for killing one or more undesirable microorganism(s) immobilized within the growth chamber of this system, without harming other desirable microorganisms contained therein.

Still further provided is a kit for use in rapidly detecting growth or metabolism of at least one immobilized microorganism.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE FIGURES

The foregoing summary, as well as the following detailed description of the invention, will be better understood when read in conjunction with the appended figures, which are not intended to be limiting.

FIG. 1B illustrates a cross-section of the hollow form chamber in FIG. 1A.

DETAILED DESCRIPTION OF CERTAIN PREFERRED EMBODIMENTS

Figure 1A:
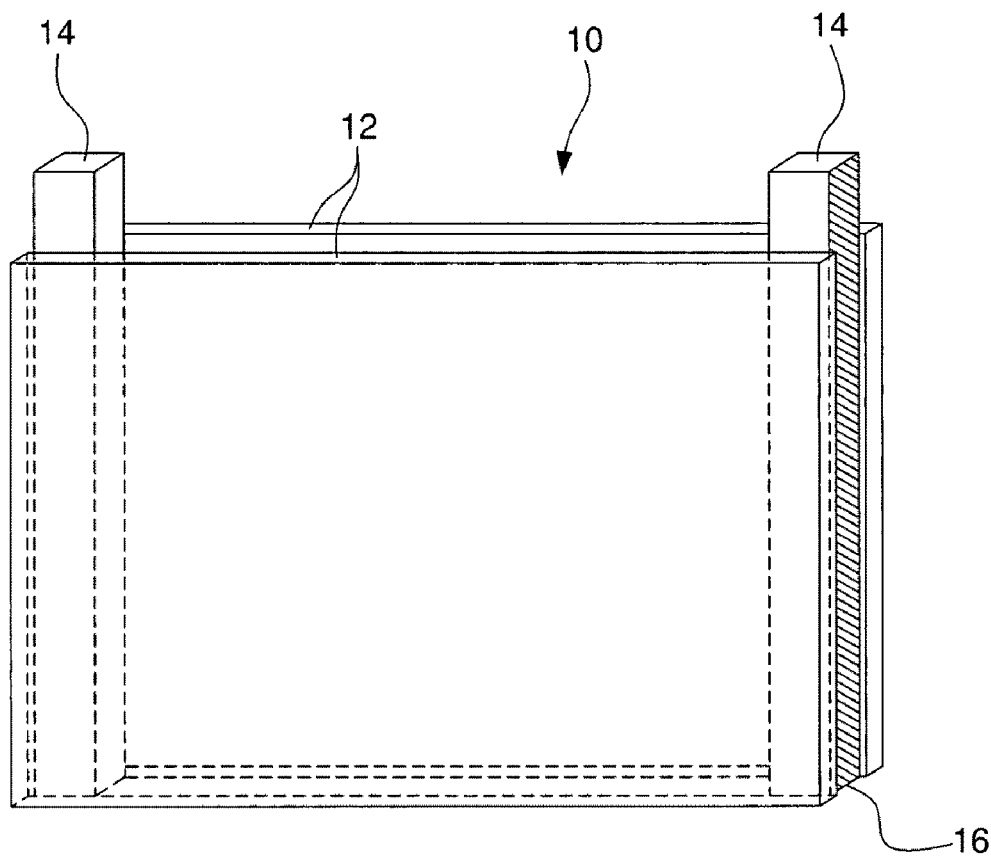
FIGS. 1A and 1B illustrate an exemplary embodiment of the hollow form (FIG. 1A) for making a gel containing a microorganism in accordance with present methods.

The present invention provides a process for the rapid and accurate demonstration of the growth of a microorganism growth in a non-liquid culture medium. Moreover, by including growth or metabolism indicators and by immobilizing the microorganism within the gel, rapid detection is facilitated, while at the same time significantly reducing the risk of contamination that often results from additional manipulation that is otherwise necessary in the slow liquid culture methods of the prior art. Accordingly, in a preferred embodiment, a gelled culture medium contains a non-toxic, water-soluble, phosphorescent compound which measures oxygen content (partial pressure) by oxygen-dependent quenching of phosphorescence, while in another, it contains a fluorescent pH indicator that demonstrates growth by pH-dependent intensity change or wavelength shift in the emission spectrum.

Because microorganisms growing in culture consume oxygen, one can detect cell growth in an inoculated medium, as compared with a sterile culture medium (e.g., without microorganisms growing in it). Thus, based upon the rate of oxygen consumption, the localized reduction of oxygen is detectable in the presence of viable microorganisms in the area adjacent to each cell or clonal colony growing in the fixed, non-liquid culture medium. It is further possible to then quantify the local rate of oxygen consumption for each particular organism. Accordingly, one or more non-toxic, water-soluble and/or otherwise physiological medium-soluble phosphorescent compounds are included in the culture medium to measure oxygen content by the oxygen-dependent quenching of the phosphorescence (partial pressure of oxygen) of the compounds. Phosphorescence is measurable following excitation of the compounds, as will be described in greater detail below. This method is useful for rapidly detecting metabolism of aerobic organisms and cells.

However, many pathogens are obligate or facultative anaerobes, and must be cultured in media that are very low in oxygen or for which the oxygen pressure is zero. All viable microorganisms produce acidic metabolites into the culture medium in the course of cell division and growth. Therefore, in a weakly-buffered fixed, non-liquid culture medium, growing cells cause a localized decrease in pH in the gel adjacent to the cells. Consequently, growth of such microorganisms is determined by the methods of the present invention by rapidly detecting a localized change in fluorescence emission in a fluorescent pH indicator, or in absorption of a color pH indicator, which thereby further indicates the location of the growing microorganism. Accordingly, in at least one embodiment designed for rapid detection of pathogen growth in anaerobic media, one or more soluble fluorescent or color pH indicator compounds are included to demonstrate the growth of acid-producing microorganisms, as will be described in greater detail below.

In yet another embodiment of the present invention, methods are provided in which the non-toxic, water-soluble and/or otherwise physiological medium-soluble phosphorescent compounds and the fluorescent compounds are compatible, and are used together in the culture medium.

Furthermore, the location of the growing microorganism is constrained in the gelled culture medium of the present invention, such that individual cells or colonies may be identified and separately collected for further manipulation. In one aspect, rapid detection of growth of a pathogen growth is provided. For example, in the case of a patient suspected of having tuberculosis, it is important to detect the growth of contagious *Mycobacteria* as early as possible, in order to quickly provide disease intervention, and to determine if isolation is required for the protection of other patients and health care staff. Advantageously, once an organism is detected, the present method provides the ability to conduct further testing of isolates of the microorganism, for example, to characterize and identify the cell, or to determine antibiotic sensitivity of the identified cells to facilitate appropriate medical treatment of the infected patient.

Advantageously the present invention permits very rapid detection of growth of the microorganisms in the inoculate. Typically the method requires only about 1-2 hours to detect growth of bacteria with rapid doubling times, and up to only about 12-72 hours for *M. tuberculosis*, which has one of the slower doubling times. The rapid detection capability results from the very high sensitivity achieved by having the oxygen-sensitive phosphor, the fluorescent pH indicator, or the color pH indicator within the gel containing the microorganisms. Thus, because the cells are in a fixed location, cell growth is detectable in the regions of the culture medium immediately adjacent to and surrounding the cell colonies as oxygen is consumed or pH changes occur. Moreover, the gelled culture medium of the present invention is easily handled, and because the oxygen-sensitive phosphor or pH indicator is contained therein, determining viability of the inoculated microorganism, and transferring and subsequent manipulation of the isolated cells or colonies is simplified.

In an embodiment of the invention, after growth or metabolism is rapidly detected, the location of the growing cell or cell colony is marked or noted, and then the individual viable clonal colony is collected and further grown as a pure clonal culture. Thus, the present method advantageously facilitates the use of any known or yet to be discovered methods for the identification and characterization of a microorganism, including but not limited to, determination of antibiotic sensitivity and DNA analysis, such as PCR or probe hybridization.

In another embodiment, the doubling time of the microorganism itself is utilized in the present methods, particularly in cultures containing a mixture of microorganisms in which it is normally very difficult to determine the growth of the overwhelmed slow-growing microorganisms. For example, the rapidly-growing organisms, such as most bacteria, are detected early, having divided several times before the slow-growing cells have doubled. Thus, if the fast-growing microorganism is the target of investigation, it may be selected before the slow-growing microorganisms begin to even form colonies. However, if the targeted cells are a slow-growing microorganism, fast-growing microorganisms in the mixed culture consume the nutrients and oxygen in the gelled culture media, masking the growth of the slower-growing cells. In that case, however, the present method makes it possible to kill the unwanted fast-growers, for example, by means of a brief burst of ultraviolet light from a collimated laser diode, clearing the gelled culture media for growth of a significantly purer population of slow-growing microorganisms.

Microorganisms

In the instant invention, a population of microorganisms in the test sample is introduced into a gelled culture medium containing the selected phosphors or fluorescent or color pH indicators. The test microorganism (also simply referred to as a "microbe" or "organism" or "cell" herein) is a single celled organism which may be found in any biological sample, such as blood, which has a low bacterial count in a large fluid volume, or urine or wound exudates having a high bacterial count in a small volume of fluid, requiring serial dilution prior to analysis. The test microorganism includes pathogenic samples from a patient, such as, but not limited to, urine specimens, matter from wounds and abscesses, or blood, tissue and sputum samples.

As used herein, "microorganism" refers to one or more organisms that may be propagated in vitro for at least about three doublings as clonal colonies of cells. This includes, for example, without limitation: bacteria, *Actinomycetales, Cyanobacteria* (unicellular algae), fungi, protozoa, animal cells, plant cells and viruses. Exemplary bacteria, without intended limitation, include species from the genera: *Bacillus, Mycobacterium, Actinomyces, Nocardia, Pseudomonas, Methanomonas, Protaminobacter, Methylococcus, Arthrobacter, Methylomonas, Brevibacterium, Acetobacter, Micrococcus, Rhodopseudomonas, Corynebacterium, Microbacterium, Achromobacter, Methylobacterium, Methylosinum, Methylocytis, Acinetobacter*, and mixtures thereof. Exemplary fungi include species from the genera: *Saccharomyces, Schizosaccharomyces, Pichia, Cryptococcus, Kluyveromyces, Sporobolomyces, Rhodotorula*, and *Aureobasidium*; and algae, e.g., *Chlorella*. Exemplary insect cells include *Spodoptera frugiperda* (e.g., Sf9 and Sf21 cell lines) and *Drosophila* S2 cells. Exemplary mammalian cells include: BHK cells, BSC1 cells, BSC 40 cells, BMT10 cells, VERO cells, COS1 cells, COS7 cells, Chinese hamster ovary (CHO) cells, 3T3 cells, NIH3T3 cells, 293 cells, HEPG2 cells, HeLa cells, L cells, MDCK cells, HEK293 cells, W138 cells, murine ES cell lines (e.g., from strains 129/SV, C57/BL6, DBA-1, 129/SVJ), K562 cells, Jurkat cells, and BW5147 cells. Transformants, transfectants, primary and secondary cell cultures, and hybridomas and other fused cells are also contemplated for use in the instant invention. Other mammalian cell lines are well known and readily available from the American Type Culture Collection (ATCC) (Manassas, Va., USA) and the National Institute of General Medical Sciences (NIGMS) Human Genetic Cell Repository at the Coriell Cell Repositories (Camden, N.J., USA).

Advantageously, the rapid detection attributes of the present invention reduce the time typically required for cell growth demonstration/identification. The inventive method is particularly suited for the rapid demonstration of growth (about 12-72 hours), even for such slow-growing tuberculosis agents as *M. tuberculosis* and *M. bovis*, and *M. avium*, which may appear in AIDS patients. As compared with the time required before cell growth is evident for the same microorganism using conventional, liquid culture methods, i.e., typically at least eight to ten weeks of incubation, detectable growth in $\leq 72$ hours is significantly more rapid.

Thus, the inventive method is also useful in monitoring the production of microorganisms in fermentation processes, which are widely used for a variety of purposes including chemical conversions, protein preparation, chemical reactions/chemical compound production, examples of which are discussed in U.S. Pat. No. 4,411,997. Such microorganisms may be either a facultative anaerobe, that is, a microbe that can switch between aerobic and anaerobic types of metabolism, or an obligate anaerobe. Non-limiting exemplary bacterial anaerobes include: *Bacteroides, Prevotella, Porphyromonas, Fusobacterium, Peptostreptococcus, Klebsiella, Entererobacter, Clostridium, Desulfovibrio, Desulfuromonas, Desuljotomaculum, Sporosarcina, Lactobacillus, Veillonella, Acidaminococcus, Methanobacterium, Methoanococcus*, and *Archaeoglobus*.

The present invention is also useful in the rapid detection of growth of potential transformants or transfectants. Transformants may be selected, for instance, by the addition of growth selection agents, including, but not limited to, antibiotics, to the culture medium.

In accordance with the methods of the present invention, the test microorganisms or microbe-containing sample selected for testing must be evenly distributed throughout the gelled medium by methods described in greater detail below. Addition of the microorganism inoculate after the liquid culture medium has gelled would not permit such distribution, thus the cells must be distributed while the medium is still in the liquid state.

Culture Medium

The present invention uses a "gelled" culture medium for the rapid detection of cell growth of a microorganism, thereby offering advantages over standard liquid culture or plating methods. As used herein, the "gel" refers to an initial liquid culture medium that is polymerized to become a solid or semi-solid matrix. As used herein, "liquid culture medium" refers to an aqueous medium that contains at least one component necessary for growth of a microorganism inoculate. Prior to formation of the solid or semi-solid matrix, the gel in the liquid state (comprising a gelling material and a liquid culture medium) is referred to herein as a "gelling culture medium."

Recognized "gelling materials" initiate the polymerization of the liquid culture medium to a gel form, and for use in the present invention must be non-toxic and compatible with cellular growth and metabolism. Such gelling materials comprise one or more than one composition or compound, which may be used singly or in combination, including natural and synthetic components. Non-limiting examples of gelling materials include: agars, agaroses, carageenans, bentonite, alginates, collagens, gelatins, fused silicates, water soluble starches, polyacrylates, celluloses, cellulose derivatives, polyethylene glycols, polyethylene oxides, polyvinyl alcohols, dextrans, polyacrylamides, polysaccharides, hydrogel powders, or any other gelling or viscosity enhancing material(s).

Some gelling materials require heating to elevated temperatures to dissolve the gelling material in the liquid culture medium, but such high temperatures would be fatal to most microorganism. Upon cooling below a critical temperature, the heated gelling culture medium will undergo gelation. However, recognizing that the cells cannot be exposed to elevated temperatures that could result in cell death or injury, the present methods require that the microorganisms are evenly distribute throughout the gelled medium. Consequently, the microorganism inoculate must be added to the liquid culture medium prior to gelation, but after the previously heated medium has cooled to a temperature suitable for cell growth. Selecting a gelling material and a liquid culture medium, along with determining suitable temperature parameters for adding the microorganisms to the liquid culture medium would, however, be well known to a skilled cell biologist.

The preferred gelling material gels at low concentrations of gelling material, and forms a three-dimensional matrix that permits the cells in the sample being tested to divide (or double) at least about three times without being physically restricted by the gel. In those embodiments requiring a larger number of cells, the microorganism should be able to grow and double at least about eight, and more preferably, at least about ten doublings. In other embodiments, it is preferred that the gel is formed from a gelling material that can be readily digested by a process that does not adversely affect subsequent growth of the included cells. The skilled artisan will know of available gelling materials and be able to select a gelling material that is suitable for growth of the microorganism or microbe(s) in the sample selected for testing.

Prior to polymerization, the liquid culture medium contains at least one component, and preferably all of the components necessary for cell division and growth of the microorganism or microbe(s) in the sample being tested. Non-limiting examples of such components include: nutrients for cells growth, hormones and growth factors, and serum. Nutrients include, but are not limited to: organic and inorganic salts, essential amino acids, peptides and proteins, fatty acids, sugars, starches, nucleic acids, nitrogen compounds, trace elements and vitamins.

In addition, the culture medium may contain, for example, but without limitation, pH buffering agents, antibiotics, selection agents, expression induction agents and agents the reduce oxygen content, such as enzyme-substrate combinations of an oxygen-consuming reaction. Such enzyme-substrate combinations include, but are not limited to: glucose, glucose oxidase and catalase, and ascorbic acid and ascorbate oxidase. Selection agents and expression induction agents are particularly useful for identifying transformants rapidly in the instant invention, and are well known to the skilled artisan. The culture medium may also be adjusted as needed for microorganism growth with regard to properties such as, but not limited to, oxygen concentration, carbon dioxide concentration and pH, as would be known to one skilled in cell growth and culture.

As additional agents, nutrients or other compounds are added to the gelled culture medium of the present invention, they may be added initially to either the gelling material or the liquid culture medium, or to both, so long as the additions are homogeneously distributed in the final gelled culture medium and are present in a form that will be usable to the cells during cell division and growth, in an amount sufficient for at least three doublings. No order of addition is implied.

As used herein, an "inoculated mixture" refers to the gelling culture medium prior to gelation, with the growth or metabolism indicator(s) and all necessary growth additives and gelling agent dissolved therein, and to which the test sample of microorganisms has been added. No order of addition of indicator and microorganism to the gelling culture medium, however, is implied. Indeed, the growth or metabolism indicator may be added to either the liquid culture medium or the gelling medium, prior to the formation of the final gel. The point at which either the indicator or the microorganisms may no longer be added to the gelled culture medium is the point at which the gel has polymerized to the extent that additions may no longer be uniformly or homogeneously dispersed throughout the medium. Until that point however, it is possible to make additions in any order, as would be readily recognized by one familiar with cell biology.

Preferably, the number of microorganisms added to the culture medium does not exceed, and more preferably is below, the maximal detection limit of the system. Estimating the maximal detection limit of the system is discussed in more detail below.

In certain embodiments, where the concentration of microorganisms in a biological sample is unknown or suspected to be large, for instance, in a urine sample, it is useful to prepare a dilution series of the sample according to know methods, using an appropriate, sterile, isotonic, aqueous solution, prior to addition to the gelling culture medium. Each dilution is then added to separate aliquots of sterile gelling culture medium in accordance with the present invention for growth and detection purposes. Such a dilution series will reduce the possibility of separate cells growing immediately adjacent to each other, which may reduce the effectiveness of the growth detection system, and the subsequent collection of individual clonal colonies.

Forming and Using the Gel Matrix

To form the gel matrix of the present invention, the "inoculated mixture," including culture medium, indicator(s) and all necessary additives to permit cell growth, metabolism and division for at least 3 or more doublings, is placed into a hollow form growth chamber, such as the exemplified forms described in greater detail below. Once the inoculated mixture undergoes gelation and has formed a solid or semi-solid matrix, it is referred to herein, interchangeably, as the "gelled culture medium" or simply, the "gel." The gelled culture medium essentially functions to immobilize each cell contained therein, such that they do not significantly move, migrate or diffuse, to the extent that more than one cell is in each growth area, while also allowing the cell to grow and divide.

A "growth area" refers the three-dimensional region or halo of nutrients, oxygen and other components within the gelled culture medium surrounding a cell, and which is consumed by that cell in the course of three or more doublings in accordance with the present methods (after three doublings, of course, a clonal colony will have formed, and it is no longer a single cell, but continued reference will be made to a cell and is meant to include any colony grown from divisions of the cell). Once the halo around one cell overlaps with the halo around another unrelated cell, the lack of available nutrients or oxygen previously consumed by another cell could disadvantageously affect the final growth analysis, depending on the reduction of necessary growth materials to the cell, and the length and extent of such reduction. Consequently, it is again a goal of the present invention to permit accurate data to be provided, that the cells within the microorganism sample must be well-spaced, without overlap of individual unrelated cells or cell colonies or the growth area around each.

The gelled culture medium also functions to keep the growing colonies of microorganisms in the sample in communicable contact with the oxygen-sensitive phosphor or fluorescent pH indicator in the gel. "Communicable contact," as used herein, means that the selected indicator is in contact with each cell or colony, or within the growth area immediately surrounding each cell or colony, such that the oxygen pressure in the growth area associated with each cell or colony influences the indicator in a detectable way.

The hollow form may be any size or shape so long as the oxygen-quenched phosphorescence or pH-sensitive fluorescence or absorption change is detectable in the gel formed therein. The hollow form serves to contain the inoculated mixture during the gelation process, forming a "growth chamber" (also referred to as a "culture chamber," or simple as a "chamber"), and in certain embodiments, also to minimize the exposure of the gel surface exposure to the air, thereby limiting contamination or diffusion of new oxygen through the outer air to gel interface. Preferably, the hollow form defines a uniform cylindrical or rectangular slab shape, which is conferred on the gelled culture medium. Cylindrical or "tube" gels may be formed, for instance, in polypropylene or glass tubing, having a diameter, preferably, of no more than about 1-3 mm. Biologically compatible, standard tubing, usually polyethylene or polypropylene, preferably clear or translucent, that is readily cut to desired lengths, is preferred to facilitate the separation of individual colonies after detection of growing microorganisms.

Figure 1B:
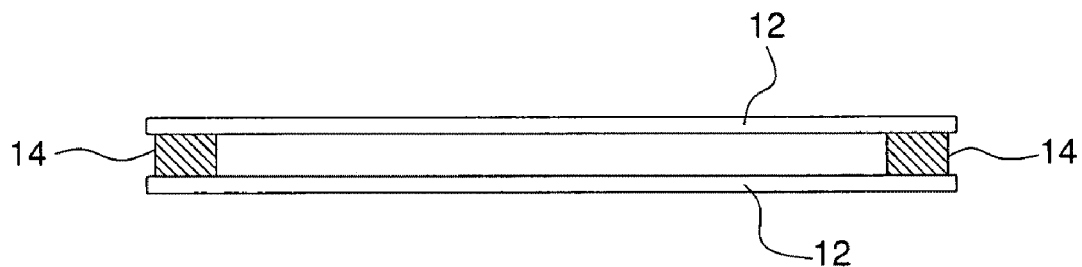

When the hollow form defines a rectangular slab shape chamber, the resulting gel in such form is referred to as a "slab gel." As shown schematically in FIG. 1A, for a rectangular slab-shaped, hollow form 10 comprises two identical planar plates 12, which are parallel to each other and are separated by side spacers 14 positioned there-between. The spacers range between 0.2 and 2.0 millimeters (mm) thick, preferably about 0.5 mm thick. The thickness is a useful variable, wherein thinner means faster detection and fewer cells in the colony when detection occurs. Accordingly, there may be occasions where higher cell numbers are desired in which case greater spacing would be desired. Thus, the thickness of the paired spacers functions to define the thickness of the gel, and also to contain the inoculated mixture within the hollow form and reduce leakage, while the mixture awaits or undergoes gelation. FIG. 1B depicts a cross-section of the hollow form of FIG. 1A, demonstrating the relative uniform thickness of the chamber space defined by spacers 14 of hollow form 10.

In an embodiment, in addition to the two side spacers 14, planar plates 12 are further separated by optional bottom spacer 16, as shown in FIG. 1A. Bottom spacer 16 may in the alternative be replaced by a means to seal the bottom edge (to keep the inoculated mixture within the hollow form chamber while the mixture gels), including but not limited to, a thin plugging layer of agar, agarose or vaseline-type material. In yet another embodiment, one or more spacers is permanently fixed to one or more of the planar plates, e.g., by gluing, welding, etc. or they are joined as initially manufactured. The side and bottom spacers are preferably aligned with the edges of planar plates 12 in assembled hollow form 10. Side spacers 14 are optionally sealed to further contain the liquid inoculated mixture while the mixture gels. During assembly, hollow form 10 is secured, for instance, by clamps to keep the plates and spacers in tight contact with each other. If the joints between the form components are sealed, the clamps may be removed during use, or in the alternative they may remain in place. A device designed to hold a plurality of assembled hollow form growth chambers is also contemplated.

In some embodiments, planar plates 12 are rigid or semi-rigid plates made of oxygen-impermeable material, while in other instances planar plates 12 are made of rigid or semi-rigid oxygen-permeable material. Glass, clear plastic, such as polycarbonate and Plexiglas®, and clear ceramic, are non-limiting examples of materials suitable for use in the plates 12 or spacers 14 and 16 in the invention. Optionally, the two planar plates 12 are not of the same material. In such an embodiment, at least one plate must permit light to pass through to excite the phosphor and detect phosphorescence, or to excite and detection of fluorescence, or to detect color change. The other plate must not interfere with either the excitation or detection steps. Moreover, when a semi-rigid plate is used to form part of the hollow form, it may in some embodiments be maintained as a plane by placing a third plate 12, that is rigid, adjacent to it. In such an embodiment, the rigid plate serves simply to keep the semi-rigid plate planar, so as to maintain the essentially uniform thickness of the gel.

In some embodiments, one or more of the internal plate surfaces is pre-treated where the plate surface contacts the gel to reduce or prevent sticking of the gel to the plate. This pre-treatment eases removal of the plate prior to removing microorganisms whose growth is detected in the gel. A silicon-based pre-treatment is a non-limiting example. Other such materials that are compatible with biological growth would be known by those well versed in the art.

Planar plates 12 need not in every case be identical in size. In some embodiments, planar plates 12 are of different lengths. The difference in lengths may assist in inserting the inoculated mixture into the hollow form chamber. Although preferably rectangular, the plates may be of other shapes, including square, circular or oval. The stands and plates used in making gels for gel electrophoresis provide a non-limiting example of the type of apparatus that could be used as a hollow form to contain the gels.

As with the formation of electrophoresis gels, the inoculated mixture is placed into a hollow form chamber in such a way as to minimize/preclude air bubble formation within the gel. The mixture is then allowed to gel, while maintaining or creating an essentially uniform or homogeneous dispersion of the microorganisms therein, so that the uniform dispersion is maintained in the solid or semi-solid gel. An essentially uniform dispersion of microorganisms in the gel will assist in identifying and collecting separate clonal colonies identified by the instant method.

The viscosity of a gelling culture medium comprising agarose is sufficient to maintain the dispersion of typical bacteria achieved by swirling the biological sample into the gelling culture medium. For other gelling culture medium, and for microorganisms of a substantially different density, it is useful to lay the hollow form containing the inoculated mixture on one of its planar plates on a level surface to help maintain the preferred essentially uniform dispersion. For a cylindrical hollow form, laying the form essentially horizontal on a level surface is useful to maintain dispersion.

The entire growth chamber (the hollow form containing the gelled culture medium which contains the immobilized microorganism and the growth or metabolism indicator) is then placed in a constant temperature incubator and maintained at the appropriate temperature for growth of the microorganism. Preferably, for photoluminescent indicators, there is minimum light exposure of the growth chamber during incubation. In some embodiments, the bottom spacer or seal is removed.

In one aspect, an exposed gel edge may be sealed with a material, including but not limited to, agar or agarose or a vaseline-type material, to reduce or prevent drying out of the edge, but this is not required. However, the smallest possible surface area of gel exposed to air is maintained to minimize the possibility of contamination or substantial oxygen diffusion into the gel, which would affect detection results.

In theory, once the medium has gelled, the cells are immobilized or "locked" into place, meaning that each is essentially fixed and cannot move within the sample relative to any other cells that may be present. Thus, each cell will consume oxygen or release acidic metabolites at only one growth area or site during incubation. As the cell divides and forms a colony, the new cells will also remain at that site (typically the cells remain in contact with each other in a clonal colony). Once a cell or cell colony is located through either the depletion of oxygen or a change in pH in its immediate environment, the slab gel can be exposed by removing one planar plate without affecting cell position of each cell within the gel. For tube gels, the gel may be extruded from the hollow form using pressure, or it may be mechanically removed.

In an alternative and preferred embodiment a capped, sterile glass or plastic growth bottle with flat sides could be used to form the growth chamber in place of the hollow form, i.e. Roux culture bottles of any size or shape, wide mouth or narrow mouth, from e.g., Bellco Biotechnology or Thomas Scientific, available from Laboratory Supply Distributors, Mt. Laurel N.J. This significantly reduces the preparation time and simplifies the elaborate filling procedures of the present invention, but commercially available "bottles" do not come in all sizes. Typically such bottles contain larger volumes than would be used in the present rapid detection method. Therefore, the space from wall to wall is greater than is presently needed. However, bottles can be specifically formed for commercial purposes for use in the present invention that have an interior wall-to-wall spacing of 0.5 cm or less, and with flat, transparent sides. Oxygen permeability of the bottle surface is controlled by the material selected, and drying-out is no longer a problem in the capped bottles. Moreover, because these bottles are self-supporting and disposable, the rapid detection system is convenient, readily reproducible, and inexpensive to operate.

Using the pre-formed bottles, the appropriate culture medium, containing the selected marker and all necessary growth additives, is collected in the sterile bottles and transported to a laboratory where the medium-filled bottles are brought above the gel temperature and the gelling agent added. Then as the temperature of the heated culture medium falls back toward ambient temperature and reaches a more cell-friendly level (e.g., 40° C. to 45° C for most cells), the microorganism sample is added and distributed prior to gelation. Typical growth temperature for cells is about 37° C. However, both the highest temperature at which a typical cell in the selected sample will survive until gelation occurs, and the optimal temperature for growth and cell division, are known to a skilled cell biologist and other practitioners. Of course, as discussed above, in the system using the hollow form chamber, the order of addition may vary as dictated by circumstances, and the bottle need not necessarily change location.

In a preferred embodiment, the bottle containing the gelled inoculation mixture is further placed in a rack, where it is periodically moved into position permitting the marker, e.g., the phosphorescence or pH marker, to be activated and viewed or imaged by a camera. In an additional embodiment, an image analysis program analyzes the image, reporting the number of colonies detected, time of detection etc, so that the system is almost fully automated and reliable.

Collection of the colonies for future identification or culture in the "bottle" embodiment requires a somewhat more sophisticated process than the above-described hollow form system, but bottles made in two pieces and clamped, snap-sealed, or glued together are adaptable for this purpose. If the glue is dissolved with a solvent or the clamps removed or the snap seal broken, the two halves of the "bottle" can be separated, effectively lifting the lid formed by one flat, transparent side from the other half of the bottle that still contains the gelled inoculation mixture. Thus, the colonies can be readily collected and/or examined.

In one embodiment, a selected growing cell, or colony of cells, or a plurality of cells or colonies, are selectively isolated by cutting out the piece of the gel in which they are growing. For instance, a tube gel formed in a hollow form made of material that can be cut is sliced to obtain a gel piece with an individual colony. Location of the cell within the selected area is detected and confirmed by the phosphorescent or fluorescent indicator. The gel piece is, in one embodiment, digested/dissolved in order to release the cell(s) for further analysis. In another embodiment, the gel piece is placed directly into liquid culture medium and the cells contained within the gel piece are allowed to continue growing.

In an alternative embodiment, the cut gel piece is gently ruptured or crushed with a sterile implement, to release, but not harm the cell(s), such as a glass rod, toothpick, metal loop or metal spatula, prior to its addition to a liquid culture medium.

In another embodiment, the colony may be "picked" or removed out of the intact gel or a gel piece using a sterile implement. The colony is then, in a preferred embodiment, transferred to liquid culture medium for growth, streaked out on a growth plate by recognized cell streaking techniques, or inserted into a storage medium, such as an agar plug or a slant. Such picking or removal may be done manually or robotically by methods known in the art.

Sterile technique and sterilization methods are well-known in the art and to the skilled artisan. See for instance Sambrook et al., supra, 1989; Ausubel et al., supra, 1997; Gerhardt et al., supra, 1994. Likewise, proper handling and containment of potentially infectious microorganisms is well-known to the skilled artisan. For instance, under federal guidelines, all facilities handling potentially infectious agents must adhere to strict procedures to insure containment of these pathogens. Depending on the ease with which microorganisms can be transmitted, they are classified as BSL-1, BSL-2, BSL-3 or BSL-4, with BSL-4 carrying the highest risk of infection.

Selecting Slow-Growing Organisms Over Fast-Growing Organisms in the Same Sample.

In another embodiment, fast-growing organisms, which often contaminate cultures for *M. tuberculosis* and other slow-growing pathogens, are detected and killed. The more rapidly-growing organisms typically overgrow the culture, eliminating, or seriously impairing, the possibility of detecting the slower-growing pathogen. Rapidly-growing organisms are easily detected earlier than slow-growing one, and can be selectively killed using brief bursts of ultraviolet light from a collimated laser diode. Ultraviolet laser diodes (e.g., 375 nm) are commercially available in which the beam can be collimated to give a diameter of 100-200 microns. The laser is used to selectively kill the undesirable, rapidly-growing colonies by hitting the core of each of the detected spots with a brief flash of ultraviolet light. Exposure to a beam for ~100 millisecond per growth spot is typically sufficient. However, the process can be repeated as necessary.

This laser treatment process can be automated and is inexpensive. Once the faster-growing organisms are eliminated, the slower-growing pathogens then appear at their characteristic time, uncontaminated by the presence of fast-growing organisms.

Cell Growth Indicator

The indicator is preferably water soluble so that it is dissolvable in the culture medium. Preferably at least one growth or metabolism indicator is a photoluminescent molecule added to the culture medium of the present invention and distributed evenly prior to gelation. The growth or metabolism indicator is a molecule that acts as a sensor in the environment (growth area) immediately surrounding the growing cell from the test sample inoculate in culture. Photoluminescent processes are divided into two different processes: phosphorescence and fluorescence. Preferably, the indicator is either an oxygen-quenchable phosphor or a fluorescent pH indicator. A pH indicator which changes color in response to changes in pH are also used. The preferred indicators are discussed in greater detail below.

Detection and Selection of Aerobic Organisms

For the detection and selection of aerobic organisms, the phosphorescence from the oxygen sensitive phosphor in the gel is imaged using a detector of infrared light, either by intensity or lifetime, at intervals of about 10 minutes to an hour. Measuring phosphorescent lifetime is not an absolute requirement of the invention. However, using lifetime measurements can eliminate most, or all, contaminating changes in fluorescence or absorption of the medium. Thus, it is the preferred detection method for most applications of the instant invention. Moreover, phosphorescence lifetime is useful for distinguishing phosphorescence from fluorescence. This embodiment is particularly useful, for instance, when identifying transformants or transfectants carrying a fluorescent marker gene, such as, but not limited to, green fluorescent protein (GFP).

As cells grow and consume oxygen, small oxygen-deficient "wells" form in the cell growth area within the gel. These oxygen-depleted "wells" are observed by the increase in phosphorescence intensity and/or phosphorescence lifetime that occurs at that location because of the decreased oxygen pressures within the well. When imaging the largest plane of the slab gel, the position of a growing cell in the gel will appear as a disk, circle or point with a central core of highest intensity/longest lifetime phosphorescence surrounded by a graded ring in which the phosphorescence intensity/lifetimes progressively decrease with distance from the central core. The size of the disk and the gradient in lifetime/intensity from the outside to the core is a measure of the rate of oxygen consumption. Since the presence of oxygen decreases phosphorescence, then the point of lowest oxygen pressure (greatest phosphorescence/longest lifetime) is nearest the cell.

As the time of culture incubation increases, the growth area disk steadily expands around each growing cell, as they continue to grow and divide. Before the cell at center of the growth area disk or sphere becomes seriously hypoxic (typically $\leq$2% to 5% oxygen, or as recognized by one skilled in the art), the well becomes quite large, about 500 microns or more in diameter. The continuous uptake of oxygen by the cell(s) lowers the oxygen in the immediate environment of the cell, causing formation of the oxygen-deficient growth area surrounding the cell. Eventually, the oxygen pressure at the center of the growth area falls to zero and the cells in the center stop growing, and eventually die. The extent of the oxygen well and its limiting diameter are functions of the rate of oxygen consumption by the cell(s) at the center of the well and the rate at which the oxygen is replenished by oxygen diffusion from the surrounding gelled culture medium. The steepness of the oxygen gradient (mm Hg oxygen/mm gel) from the core to the edge is a measure of the diffusivity of oxygen in the medium. Growth of a typical cell is not inhibited until the oxygen pressures at the central point approaches zero, meaning less than about 3 mm Hg.

Without wishing to be bound by theory, it is believed that the extremely rapid and sensitive detection of the instant invention is due to the limited oxygen supply available to the cells as a result of the immobilization within a gel. As discussed above, oxygen is consumed in the immediate area around a growing cell in the gelled culture medium. While oxygen from outside the immediate location of the growing cell will, to some extent, diffuse into the area, the rate of diffusion is limited by the properties of the gel matrix itself. Exposure of any surface of the gel to air is also preferably minimized, thereby reducing the replenishment of oxygen to the gel. Consequently, during metabolism the invention is designed so that a growing cell utilizes only the limited supply of oxygen in its immediate environment to replace the consumed oxygen.

The sensitivity of the system, defined as the minimum time needed to detect a cell's position in the gel, thus increases with decreasing separation of the plates, and thus with decreasing thickness of the gel. For instance, typical bacteria are much smaller than the thickness of a 0.1 to 2 mm gel. As the plates get closer together, the volume of gelled culture medium available to replenish the oxygen used by the cell decreases, and the oxygen diffusion gradient transitions from spherically symmetrical to planar. In a thicker gel, oxygen diffuses from three dimensions into the region surrounding the growing cell, thus there is a spherical oxygen supply. As the gel is made thinner, however, as in a preferred embodiment, the volume of gel from which the oxygen diffuses approaches a two-dimensional circle around the cell. This dramatically restricts the amount of oxygen available, thus leading to more rapid detection capabilities, but shorter cell life unless the spent nutrients and oxygen are replenished.

When using glass plates (not oxygen permeable), and gels about 200 to 500 microns thick, every organism growing in the sample is detectable within a few hours. For typical bacteria, the time to detection is less than about 120 minutes, whereas for slow-growing *Mycobacteria*, the time to detection will be on the order of a few hours to a day.

The use of oxygen-sensitive phosphors also contributes to the high sensitivity of the system. Such phosphors have a large phosphorescence intensity/lifetime increase (e.g., about 10-100 fold) as the oxygen partial pressure decreases.

As discussed above, the time to detection is directly related to the amount of oxygen in the surrounding medium. The amount of oxygen in the surrounding medium is a function of not only spacing between the plates, but also the respiratory rate of the microorganism. Accordingly, the faster the cells consume oxygen, the more quickly they are detectable. When the plates are separated by 1 mm, for example, the volume of gelled culture medium within 1 mm of a cell or colony is approximately 3 µl, whereas if the plate separation is 0.2 mm, this volume is decreased to about 0.6 µl. A greater volume of the gelled culture medium means the growing colony has a greater volume of oxygen to draw from. Therefore, the reduction in oxygen pressure, and thus, the detectable increase in phosphorescence is slowed. Equally importantly, the direction from which oxygen diffuses to the cells becomes more restricted in thinner gels, further increasing the sensitivity with which microorganism growth is detected. For instance, further decrease in the spacer thickness to 0.15 or 0.1 mm would decrease the volume within 1 mm of the cell even further, to approximately 0.45 and 0.3 µl, respectively.

In some embodiments, the reduction in gel thickness is limited by the size of the biological sample to be tested, thus by the expected concentration of microorganisms within the biological sample to be tested. For instance, in blood, the number of pathogens is likely to be quite low. Consequently, one would prefer to test a large volume of such a biological sample to assure statistically relevant results. A larger gel volume, and thus gel thickness, may therefore be required to accommodate testing of a large volume of biological sample having a low count of microorganisms, such as a blood sample. Alternatively, to accommodate a larger gel volume, one may prepare a hollow form having larger length and/or width dimensions, but using the same thickness spacers 14, as used on much smaller gels. See also Example 4.

The number of microorganisms inoculated into the gelling culture medium preferably should not exceed the maximal number that can be detected individually in a gel, given its length and width dimensions. Two cells that overlap or are "stacked" upon each other in the three-dimensional thickness of a slab gel, will likely not be detected as two separate colonies. Thus, in a thin slab gel as preferred in the present invention, the maximal detection number is dictated by the surface area of the gel used. For instance, the surface area of a 16 cm×16 cm slab gel is 256 cm$^2$. Assuming each cell/colony will occupy approximately an area of 0.2 cm×0.2 cm (0.04 cm$^2$), the maximal colony count that would allow retention of the ability to select individual colonies is approximately 6,400 (256÷0.04).

By "occupy" is meant the approximate growth area of a cell or cell colony within the gel from which oxygen is drawn; 0.2 cm measured width of the well is sufficient for the oxygen decrease in the middle of the well to provide a readily-detected spot of increased phosphorescence for unambiguous identification of a growing microorganism. Thus, for a gel having a length and width of 16 cm×16 cm, no more that about 6400 microorganisms are inoculated into and homogeneously dispersed throughout the gelling culture medium, regardless of the thickness of the hollow form (because in thicker gels they will still overlap in the same plane). Preferably fewer microorganisms are inoculated to avoid overlapping of the oxygen-depleted volumes or wells associated with the colonies.

A dilution series can be used, as discussed previously. The length and width dimensions of the hollow form (and hence the dimensions of the growth or culture chamber) can be altered by the skilled artisan in light of the present disclosure as needed for each application. The minimal desired count of detected individual colonies will be set by statistical/contamination considerations, but could be as low as 10 colonies per biological sample.

Advantageously, this new system may be automated, permitting detection of organisms down to the statistical limit in number of organisms per sample, while allowing subsequent collection of the individual colonies for further growth and evaluation.

Detection and Antibiotic Sensitivity Determination for Aerobic Pathogens

With the very fast detection system described above using glass plates, oxygen availability for cell growth is sufficiently limited that the individual colonies will grow only to a small number of cells. Although speed of detection is a significant advantage, in other embodiments, when it is necessary to know the antibiotic sensitivity of the organism, it is advantageous to grow the colonies to a larger number of cells over a longer period of time. This can be achieved by replacing the glass or thick plastic plates with thin, oxygen permeable plastic plates that provide a renewable oxygen source, but with limited maximal flux.

While detection of the growing colonies will not be as rapid in this embodiment, the greater oxygen supply allows for growth of a larger size colony. Advantageously, the larger colony size will allow for further analysis, such as antibiotic sensitivity testing, without requiring an intermediate growth step. The larger number of cells in the colony, ranging from as many as 200 cells, up to 500 cells, or even 1,000 cells, for example, will allow each colony to be removed, diluted into liquid culture medium and aliquots can then be immediately plated on antibiotic-containing media. For instance, a colony of about 500 cells could be divided and plated in duplicate on 5 different plates, thereby permitting 4 plates, each containing a different antibiotic in the medium, plus 1 control plate, to be tested. In that case, there would be about 50 organisms per plate. Thus, each plate would have enough microorganisms present to permit each set of results to be statistically reliable.

Advantageously, therefore, such methods of the present invention shorten the overall time required to characterize each individual colony, thereby accelerating detecting the organism and determining appropriate treatment for the patient infected by the microorganism. The oxygen-sensitive phosphorescence indicators provide the preferred method of sensing cell growth in the detection system for aerobic microorganisms.

Detection and Antibiotic Sensitivity Testing for Obligate Anaerobes (e.g., Pathogens)

In yet another embodiment of the invention, the above-described system using oxygen-impermeable plates or tubes to form the hollow form and contain the gel is modified to further include an oxygen-consuming reaction in the culture medium. For example, the oxygen consuming reaction could be the addition of glucose, plus glucose oxidase and catalase (to remove the resultant hydrogen peroxide), or ascorbate, plus ascorbate oxidase, in the gelling medium. The substrate and enzyme catalyzing the oxygen consumption are added immediately before gelation of the culture medium. The components are mixed into the liquid culture medium and also mixed with a sample of the microorganisms and an indicator (either a water-soluble, non-toxic fluorescent pH indicator or a water-soluble, non-toxic color pH indicator), is then injected between the oxygen-impermeable plates 12. For this embodiment of the invention, the plates are made of oxygen-impermeable materials, such as glass, plastic, or ceramics. The reaction rapidly consumes the oxygen in the medium, providing the oxygen-free environment required for growth of an anaerobe.

A fluorescent pH indicator is preferred when the pH of the system is determined by establishing a ratio of emission signals at different wavelengths. It is also effective when a large change in fluorescence/absorption intensity is associated with a change in pH. Either type of pH-sensitive fluorescent indicator will respond to a change in the local pH, and therefore, in a manner analogous to oxygen depletion by aerobes described above, the fluorescence/absorption pattern pinpoints the position of each growing cell, based upon the change in pH in its immediate environment resulting from its metabolism.

In a preferred formulation, the fluorescent pH indicator is bound to the gelling agent itself, or to a molecule of low diffusive capability in the gel, such as dextran. In another embodiment, the fluorescent pH indicator itself is a molecule having low diffusive capability in the gelled medium. In any case, maximal sensitivity is attained with very weakly buffered growth media. Advantageously, fluorescent pH indicators are available that cover a range of pKas.

The selection of the fluorescent pH indicator is based upon the growth conditions associated with the selected microorganism in the test sample that is inoculated into the gelling culture medium. Preferably, the pKa of the pH indicator is in a neutral pH range, e.g., about pH 5 to 8, more preferably at about pH 6.5 to 7.5.

The terms "pH-sensitive fluorescent compound" and "fluorescent pH indicator" are used interchangeable herein to refer to a compound in which the level of fluorescence or fluorescent wavelength is affected by pH. Thus, a change in pH in the culture medium used to support cell growth is directly related to a change in fluorescence. Non-limiting examples of pH-sensitive fluorescent compounds include: 2',7'-bis-(2-carboxyethyl)-5(and6)-carboyfluorescein (BCECF), fluorescein-isothiocyante (FITC) derivatives, such as N-(fluorescein thio-ureanyl)-glutamate (FTUG) and 8-hydroxy-1,3,6-pyrenetrisulfonate (pyranine), SNARF® indicators, fluorinated analogs of fluoresceins, such as Oregon Green® 514 carboxylic acid and Oregon Green® 488 carboxylic acid, and 5-(and 6-)carboxy-2',7'-dichlorofluorescein.

In an alternative embodiment, color pH indicators are used. The change in color, which occurs in visible wavelengths, is imaged using absorption. The color pH indicator is necessarily water-soluble and non-toxic to the growing cells. It has low level of diffusion in the gelled culture medium, or it is bonded to a molecule that has low diffusivity. The molecule may also be the gelling material.

As above, the choice of the color pH indicator is based upon the growth conditions associated with the selected microorganism in the test sample that is inoculated into the gelling culture medium. Preferably, choice of color pH indicator is made based on the growth conditions of the organism to be inoculated into the gelling culture medium. Preferably, the pKa of the pH indicator is near the pH optimum for growth of the cell/organism of interest. Typically this would be in a neutral pH range, e.g., about pH 5 to 8, more often at about pH 6.5 to 7.5.

Phosphorescence

In a well understood process, emitted light from an excited species which persists after excitation (using e.g., known methods) has ceased, is referred to as "phosphorescence," or afterglow. This persistence after excitation is a significant difference between phosphorescence and fluorescence, and reflects the underlying difference in excited states between the two. Fluorescence is emitted when a molecule in a singlet excited state returns to the ground state with emission of a photon. In phosphorescence a molecule in the excited triplet state returns to the ground state with emission of a photon. The latter, but not the former, is a "spin forbidden" transition. As a result the former (fluorescence) typically has lifetimes of less than 10 nanoseconds, whereas the latter may have lifetimes of hours. The phosphors of greatest usefulness for the present application have lifetimes from a few microseconds to a few milliseconds.

In accordance with preferred embodiments of the present invention, one or more water-soluble, non-toxic phosphorescent compounds ("phosphors") are mixed with, or are otherwise dissolved in, a gelling culture medium, which is further inoculated with microorganisms. Following gelation, the gelled culture medium and distributed sample of microorganisms are, thereafter, exposed to a light source to excite the phosphor. Thus, the present method provides a rapid and highly sensitive optical method of detecting changes in phosphorescence intensity that is directly related to qualitative differences in oxygen concentration in gelled culture medium.

Quenching of phosphorescence by oxygen follows the Stern-Volmer equation as described, for example, in U.S. Pat. Nos. 5,279,297, 6,165,741, 6,274,086, 6,362,175, and 6,701,168:

$$I_o/I = \tau_o/\tau = 1 + k_Q \times \tau_o \times pO_2 \quad \text{(Equation 1)}$$

wherein, $I_o$ and I are the phosphorescence intensities (at zero oxygen and as measured at oxygen pressure $pO_2$, respectively) and $\tau_o$ and $\tau$ the phosphorescence lifetimes in the absence of oxygen (when the oxygen pressure is zero) and at the oxygen pressure, $pO_2$, in the environment of the phosphor. As used herein, the subscript "o" designates the intensity "I" and lifetime ($\tau$) when there is no oxygen in the phosphor environment (the absence of oxygen). On the other hand, $k_Q$ is a second order rate constant related to the frequency of collisions of excited state phosphor molecules with molecular oxygen. Thus, the equation is used to convert the phosphorescence lifetime into the oxygen pressure.

Phosphorescence may be measured by any available means in accordance with the present invention. For quantitative oxygen measurements, however, phosphorescence lifetime is measured because this eliminates most of the optical interference (fluorescence, absorption, etc). U.S. Pat. No. 6,165,741, for instance, provides information on quantitative measurement of oxygen levels using oxygen-sensitive phosphors, using either the pulse method or the phase method. Phosphorescence intensity, however, is a good qualitative measurement of oxygen, and is preferred for detecting growth of microorganisms in the inventive method.

Phosphorimeters and Fluorimeters

The light source is any of several difference devices. In a preferred mode, the light source used to excite and detect phosphorescence is a light-emitting diode (LED) or a laser diode, where the latter is a special case of the former. More preferably, the excitation light source is a high power LED(s) to illuminate the gel with as uniform as possible light. The wavelength is selected to be suitable for excitation of the phosphor in the gelled culture medium, typically 450 nm for Oxyphor-G2-based phosphors. The photodetector (described more fully below) is filtered to eliminate all light of wavelengths less than the emission wavelength of the phosphor. For instance, for Oxyphor-G2-based phosphors, the camera is filtered to eliminate wavelengths less than 750 nm. The illuminating light is preferably turned on only while imaging the gel to minimize the light exposure of the system. For the same reason, the plates are preferably incubated in the dark between phosphorescence measurements to avoid long term exposure to high light intensity. There is a very low, but detectable, oxygen consumption when the phosphors are illuminated and this might result in progressive decrease in oxygen pressure in the gel if the excitation light remains on all the time.

The device used to excite and detect fluorescence, a fluorimeter, operates in a manner that is essentially the same as the phosphorimeter described above, except that it has the appropriate filters to provide the correct excitation wavelength and to detect fluorescence emission wavelengths, as would be known in the art. Visible wavelength imaging devices are used to detect changes in absorption when a color pH indicator is used.

Measuring Phosphorescence and Fluorescence Emission

To measure phosphorescence, the phosphorescence is collected, passed through appropriate filters and carried to the detector. Similarly fluorescence may be collected, and detected. Any detection system that can generate a two dimensional map of the phosphorescence intensity or lifetime, fluorescence intensity or emission, or absorption changes, can be used. The photodetector (PD) is, for instance, a photomultiplier, an avalanche photodiode or a photodiode. The PD is preferably a high resolution infrared or near infrared camera. A preferred design is an ISG-750 intensified CCD camera (ITT Industries, White Plains, N.Y.) or an on-chip amplifier CCD array-based camera (E2V Technologies, Chelmsford, UK).

Water-Soluble, Oxygen-Quenchable Phosphorescent Compounds

Water-soluble, oxygen-quenchable phosphorescent compounds (phosphors) useful in the present invention are described, for example, in U.S. Pat. Nos. 4,947,850, 6,165,741, and 6,362,175, which are herein incorporated by reference. In such phosphors, the phosphorescent chromophor, e.g., PdPorph and PtPorph, is the phosphorescent portion of the phosphor that can be converted to the triplet state (T) by light absorption, followed by a return to the ground state yielding light emission, or phosphorescence.

For phosphors to be suitable for use, inter alia, in determination of microorganism growth and identification in the present invention, the phosphors must be non-toxic to the microorganisms, or of negligible toxicity. The phosphors should also be of sufficient solubility in the gelling culture medium, that oxygen molecules can reach the growing microorganisms, permitting adequate quenching of the phosphorescent emission to provide for reliable and accurate oxygen measurements, indicating measurable growth of the sample microorganism.

A class of phosphors particularly suitable for oxygen measurement and concomitant microorganism growth identification in accordance with this invention was reported in Vinogradov and Wilson, *J. Chem. Soc., Perkin Trans.* 2:103-111 (1995), and in U.S. Pat. No. 5,837,865, which is a continuation in part of U.S. Pat. No. 6,362,175, each of which is incorporated by reference herein. The phosphors are complexes of Group VIII metals, such as Pd and Pt, with porphyrins or extended porphyrins, such as, for example, tetrabenzoporphyrin, tetranaphthaloporphyrin, tetraanthraporphyrin and various derivatives thereof. Pd complexes of tetrabenzoporphyrins and tetranaphthaloporphyrins are especially desirable. Further, Pd tetrabenzoporphyrins (PdTBP) and their derivatives have been shown to have long-lived phosphorescence (~250 millisecond) with quantum yields of 8-10%.

More preferred for use in the present invention are dendritic derivatives of the aforementioned phosphors, which are highly efficient and highly soluble phosphorescent compounds surrounded by an inert globular structure. A non-limiting example is derivatized PdTBD surrounded by a three-dimensional supramolecular structure known as a dendrimer. Such compounds are described, for example, in U.S. Pat. No. 5,837,865, above.

Dendrimer phosphors useful in this invention are three-dimensional, supramolecular, radially-symmetrical molecules comprised as an initiator-functionalized core, which in the present invention are oxygen-measuring phosphors, with interior layers attached to the core. The interior layers comprise, for example, three or four arms wherein each arm is composed of repeating units, and the layer of repeating units in each arm is considered to be a generation of the dendrimer. The outermost generation typically contains terminal functional groups, such as a primary amine attached to the outermost generation. The size and shape of the dendrimer molecule, and the functional groups present therein, can be controlled by the choice of the initiator core, the number of generations, and the nature of the repeating units employed at each generation.

At least two methods are known for the synthesis of dendrimer polymeric structures: the convergent growth approach and the divergent growth approach. Both are contemplated for use in the production of phosphors useful in the present invention.

Other references relating to dendritic macromolecules and their methods of production can be found, e.g., in U.S. Pat. Nos. 4,568,737; 5,041,516; 5,098,475; 5,256,193; 5,393,795; 5,393,797; and 5,418,301, the entire disclosures of each of which are incorporated herein by reference.

As described below, one-, two-, and three-layer polyglutamate dendritic cages synthesized divergently around novel, derivatized metallo-extended porphyrin oxygen-measuring phosphor compounds result in phosphors which are highly water-soluble in a wide pH range and display narrow distribution of phosphorescence lifetimes in deoxygenated water solutions. As further shown below, the combination of the phosphor derivatives with dendrimers, which are used as the phosphor's surrounding environment, provides a class of phosphorescent probes for accurate and reliable oxygen measurements in gelled culture medium for reliable and fast culture growth detection and identification.

The dendritic phosphors are prepared from phosphors described in U.S. Pat. No. 6,362,175; and Vinogradov and Wilson, supra, 1995, and, preferably, are of the following formula:

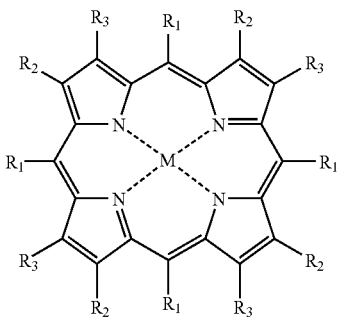

(Formula I)

wherein $R_1$ is hydrogen or substituted or unsubstituted aryl; $R_2$ and $R_3$ are independently hydrogen or are linked together to form substituted or unsubstituted aryl; and M is $H_2$ or a metal. When $R_2$ and $R_3$ are linked together to form an aryl system, the aryl system is necessarily in a fused relationship to the respective pyrrole substrate.

M is preferably a metal selected from the group consisting of Lu, Pd, Pt, Zn, Al, Sn, Y and La, and derivatives thereof, with Pd, Pt and Lu being most preferred. Non-limiting examples of suitable metal derivatives include, Pd tetrabenzoporphyrin (PdTBP), Pd tetraphenyltetrabenzoporphyrin (PdTPTBP), and PtTBP, PtTPTBP, LuTBP and LuTPTBP and naphthaloporphyrins, such as, for example, LuTNP and PdTPTNP, all of which are described in U.S. Pat. No. 6,362,175.

In certain preferred embodiments, the phosphors are tetrabenzoporphyrin (hereinafter "TBP") compounds, which correspond to the compound of Formula I above, wherein vicinal $R_2$ and $R_3$ groups are linked together to form benzene rings which are fused to the respective pyrrole rings. Also preferred are tetranaphthoporphyrin (hereinafter "TNP") and tetraanthraporphyrin (hereinafter "TAP") compounds wherein vicinal $R_2$ and $R_3$ groups are linked together to form naphthalene and anthracene ring systems, respectively. As with the fused benzene rings, the naphthalene and anthracene ring systems are fused to the respective pyrrole rings. Unless indicated otherwise, or unless apparent from the disclosure, further reference herein to "TBP" compounds is understood to refer also to regular porphyrins, TNP and TAP compounds.

Preferred TBP compounds have the following formula:

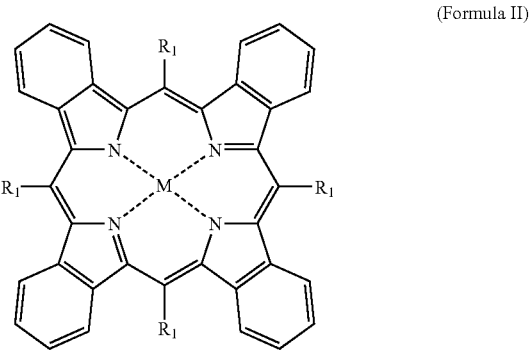

(Formula II)

wherein $R_1$ and M are as defined above. Particularly preferred TBP compounds are metallotetrabenzoporphyrin (hereinafter "MTBP") compounds where M is a metal or metal derivative as described above.

Particularly preferred among the TBP compounds are the compounds of Formula I above, wherein at least one of $R_1$ is substituted or unsubstituted phenyl. These compounds are referred to hereinafter as phenyltetrabenzoporphyrin (hereinafter "PhTBP") compounds. Preferred PhTBP compounds include substituted or unsubstituted tetraphenyltetrabenzoporphyrin (hereinafter "TPTBP") compounds, including mesotetraphenyltetrabenzoporphyrin (hereinafter "m-TPh-TBP") compounds, which have the following formula:

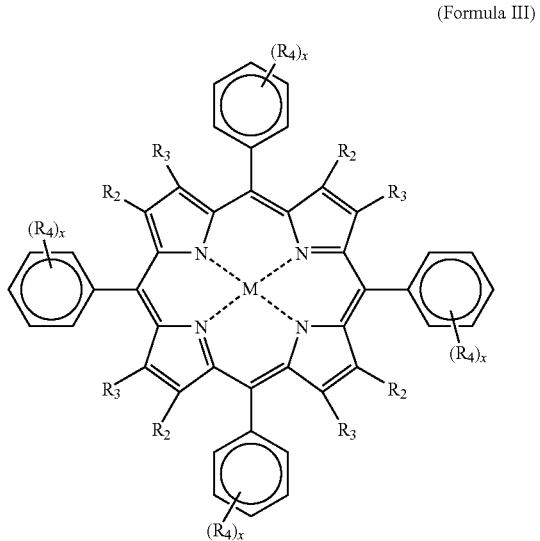

(Formula III)

wherein $R_2$, $R_3$ and M are as defined above, $R_4$ is a substituent group, and x is an integer from 0 to 3. Particularly preferred TPTBP compounds are substituted compounds of Formula III, where x is an integer from 1 to 3.

With respect to preferred substituted compounds of the invention, substituent groups are desired which impart such desirable properties to the compounds as solubility in polar solvents, including aprotic solvents, such as dimethylformamide (DMF), acetone and chloroform ($CHCl_3$), and protic solvents, such as water. The degree of substitution and the nature of the substituent groups may be tailored to obtain the desired degree of solubility, as well as solubility in the desired solvent or solvent mixture.

The phosphors useful in the instant invention are preferably not heat labile. In some embodiments, a phosphor will require an additional component to provide the appropriate oxygen quenching constant for use in the instant invention. For instance, Oxyphor G2 requires bovine serum albumin (BSA). Binding of BSA to Oxyphor G2 restricts access of oxygen to the excited triplet state, thus decreasing oxygen sensitivity and lowering the quenching constant from about 4000 to about 400. The lower quenching constant allows much more sensitive measurements due to the stronger intensity signal, while retaining a large intensity increase when oxygen pressure decreases. However, there are other phosphors also suitable for use in the instant invention, which do not require the addition of BSA. For instance, dendrimers, depending on their design, can have the same effect on the quenching constant as binding to BSA. These phosphors have dendrimer coats that are more tightly folded, and the exterior is coated with an inert coat, such as polyethylene glycol. Their quenching constants can be selectively set to values from 4000 to less than a 100. See, for instance, U.S. Pat. Nos. 5,837,865 and 6,362,175.

Devices and Kits

The invention further comprises a growth chamber device for use in the inventive method of rapidly detecting growth or metabolism of a microorganism. The growth chamber device includes a hollow form and/or bag having a longitudinal dimension and defining a space, and an aqueous gelled material within the hollow form or bag. As used herein, the term "hollow form" broadly encompasses not only the solid assembled form for shaping and containing the gelling material or inoculated mixture until gelled, but it also encompasses preformed hollow form as described herein and a sterile bag such as described in Example 3, which may be added to the fixed hollow form or used alone. All will be included by the use of the term "hollow form," as will any other means used to shape and contain the liquid gelling material or inoculated gelling material until formed into a gel.

The gelled culture medium containing a microorganism and one of a dissolved oxygen-quenchable phosphorescent compound and a dissolved fluorescent or color pH indicator is located within and fills the space in the hollow form. In a preferred embodiment, the growth chamber device further includes two parallel plates that define a longitudinal plane of the space within the hollow form, and spacers between the two planar plates, such that a rectangular space is defined.

Figure 2A:
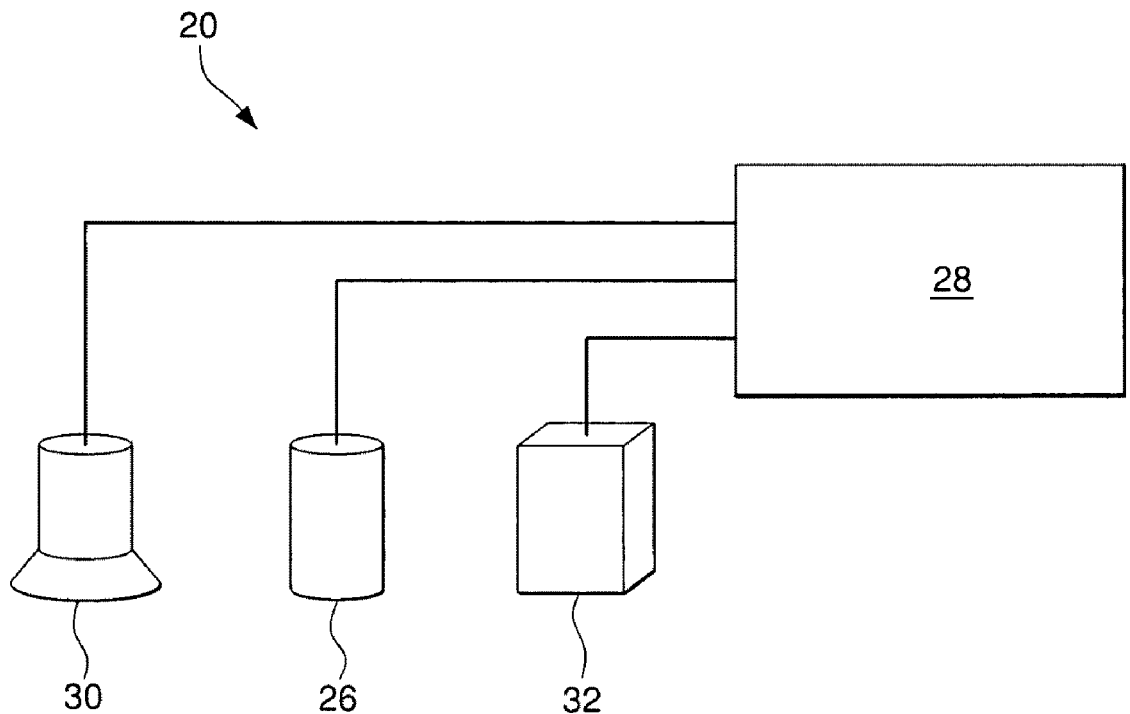
FIGS. 2a and 2b are schematic diagrams of exemplary embodiments of a device useful in the inventive method.
Figure 2B:
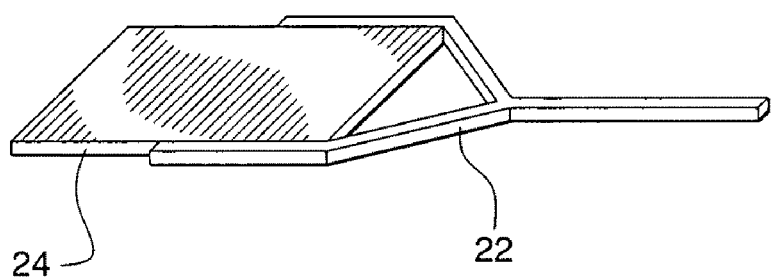
Figure 3A:
FIGS. 3A-3D are images of phosphorescence intensity of bacterial growth in a gelled culture medium. Images were taken at 30 minutes (FIG. 3A), 35 minutes (FIG. 3B), 105 minutes (FIG. 3C) and 120 minutes (FIG. 3D) after inserting the cell-inoculated mixture into the rectangular hollow form growth chamber.
Figure 3B:
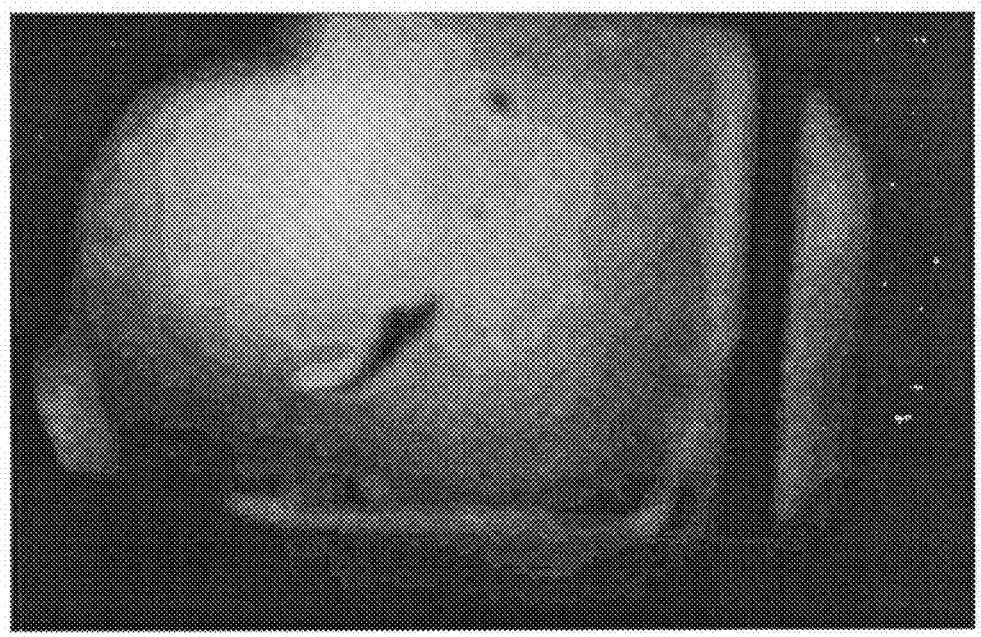
Figure 3C:
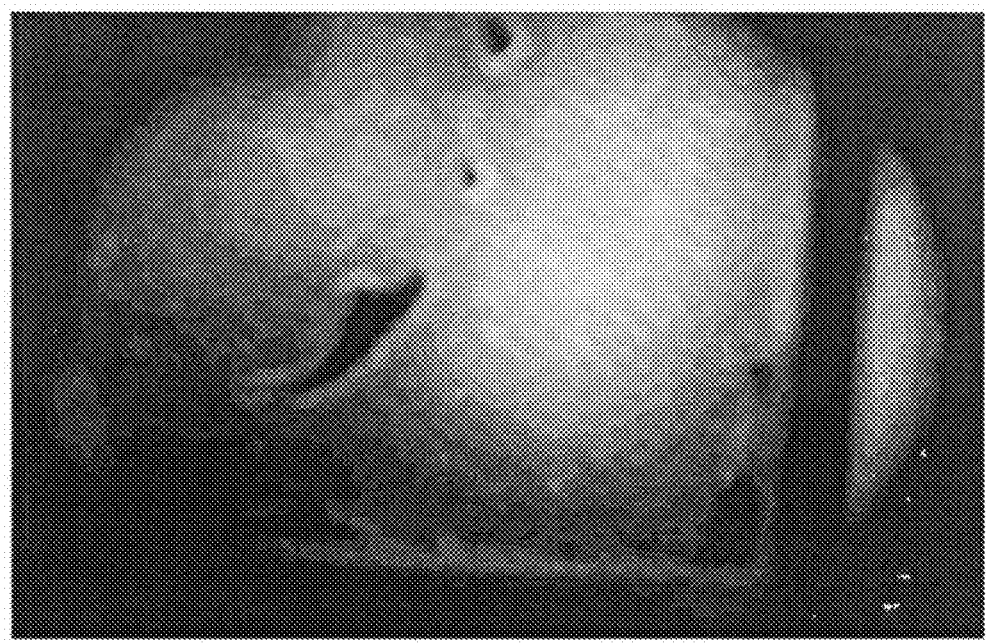
Figure 3D:
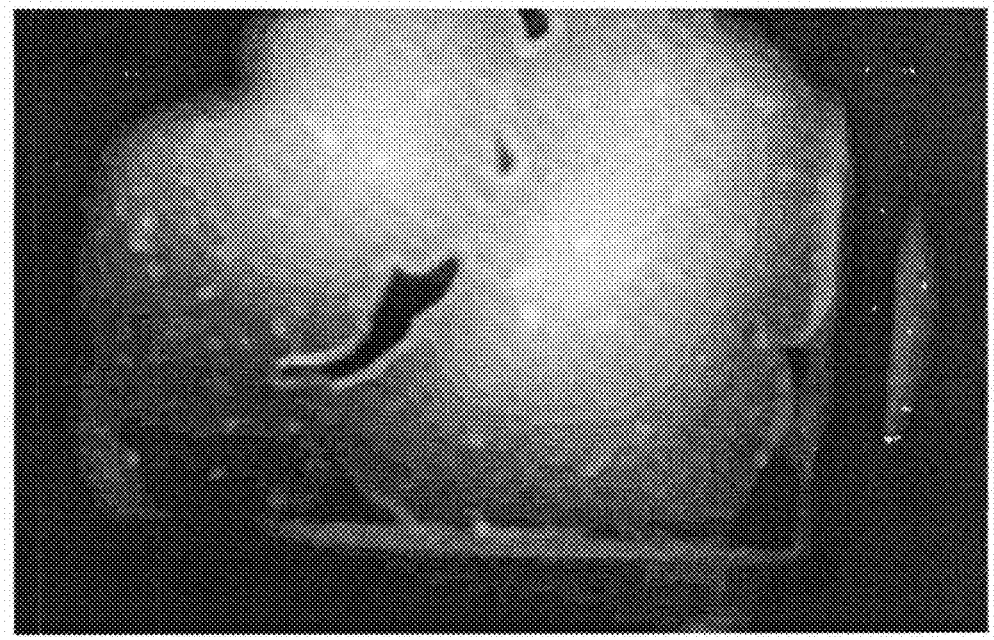
Figure 4:
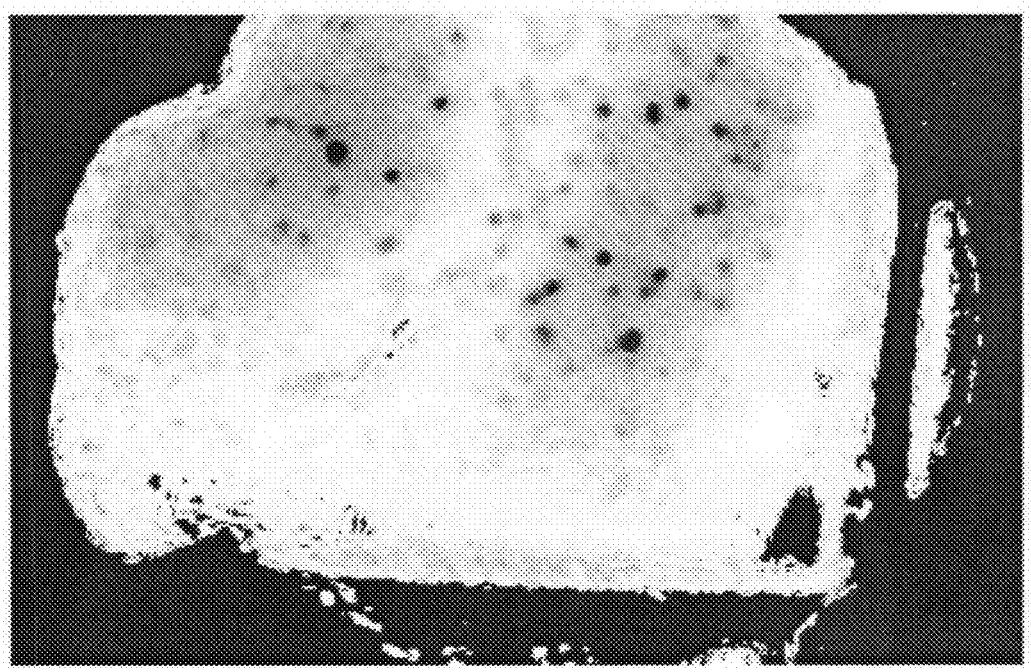
FIG. 4 is an image of an oxygen pressure map, taken at 105 minutes incubation of the same gel shown in FIG. 3C.

The invention further comprises a device to eliminate selectively individual colonies in a growth chamber device. The selective elimination device is particularly useful in embodiments of the inventive method in which faster-growing organisms are killed early to prevent them from overgrowing slower-growing organisms. As schematically illustrated in FIG. 2, device 20 includes a means 22 for holding and precisely positioning growth chamber device 24 relative to collimated laser diode 26. Collimated laser diode 26 is operably connected to processing means 28. The device further includes excitation light source 30 and detector 32, both of which are operably connected to processing means 28.

In one embodiment, the phosphorescent (or fluorescent) image detected by the detector is associated with a coordinate system, such that the location of a detected organism has precise coordinates. The processing means then uses these coordinates to aim the collimated laser diode precisely at the detected organism and activate the collimated laser diode briefly for a time sufficient to kill the detected undesirable organism or colony, without harming the surrounding desirable microorganisms. In another embodiment, an addition component, an aiming laser, is used. An aiming laser is a weak light of a wavelength detected by the detector and which is co-aligned with the killing laser. This way, the aiming laser is aimed so that its illumination spot is exactly on the growth of interest, and then collimated laser diode 26 is turned on for the required time to kill the growth thus illuminated.

As described under "Phosphorimeters and Fluorimeters," excitation light source 30 is preferably a light-emitting diode or a laser diode. Detector 32 is a photodiode, photomultiplier or an intensified CCD array. Processing means 28 is a computer capable of collecting data and processing it according to an algorithm. Positioning means 22 holds or secures growth chamber device 24 precisely, such that collimated laser diode 26 may be aimed at specific locations, either derived from the coordinate system of detector 32, or indicated by the use of an aiming laser as described. Preferably the longitudinal plane of growth chamber device 24 is held perpendicular to the laser beam of collimated laser diode 26. Positioning means 22 may be a plate or plane on which growth chamber device 24 is placed. Some embodiments further contain clamps, clips, elastic bands or similar restraining mechanisms to secure the growth chamber device and prevent or reduce its movement. Alternatively, the positioning means comprises a slot into which growth chamber device 24 may be snugly fit or a two-pronged fork that grips the growth chamber device securely, such as that which is shown schematically in FIG. 2.

The invention also includes a kit for practicing the inventive method and instructional material providing detailed direction for use of the kit. In one embodiment, this kit comprises a gelling material (preferably sterile), suitable for immobilizing a microorganism, at least one of a water-soluble, non-toxic oxygen-quenchable phosphor or a water-soluble, non-toxic fluorescent pH indicator or color pH indicator, and optionally, a hollow form. The hollow form is used for forming and containing the gel which has the gelled culture medium, the immobilized microorganism and the oxygen-quenchable phosphor or fluorescent pH indicator. The form may be sterilizable permitting reuse or fitted with a culture bag as described below.

As used herein, an "instructional material" includes a publication, a recording, a diagram, or any other medium of expression which may be used to communicate the immobilization of a microorganism in a gelled culture medium comprising one of a water-soluble, non-toxic oxygen-quenchable phosphor or a water-soluble, non-toxic fluorescent pH indicator, and the method of detecting growth or metabolism of the microorganism. The instructional material of the kit of the invention may, for example, be affixed to a container which contains the gelling material and/or the oxygen-quenchable phosphor, fluorescent pH indicator, or color pH indicator, or it may be shipped together with a container containing the gelling material and/or the oxygen-quenchable phosphor, fluorescent pH indicator, or color pH indicator. Alternatively, the instructional material may be shipped separately from the container with the intention that the instructional material and the composition be used cooperatively by the recipient.

Additional objects, advantages and novel features of the invention will be set forth in part in the description and examples which follow, and in part will become apparent to those skilled in the art on examination of the following, or may be learned by practice of the invention. The following examples, however, are understood to be illustrative only and are not to be construed as limiting the scope of the appended claims.

EXAMPLES

Example 1

Toxicity evaluation for individual growth or metabolism indicators in accordance with the invention was conveniently carried out as follows. Phosphor powder, Pd-meso-tetra (4-carboxyphenyl) porphyrin with two layers of glutamate dendrimer, was dissolved in five milliliters of distilled, deionized and filter-sterilized water and filtered through an 0.2 micron filter to provide a filter-sterilized solution with a concentration of 8 mM and a pH of 7.4. Three dilutions were made from the 8 mM solution to create stock solutions, such that an equal volume of each stock solution was used to dilute to the final concentration in the culture medium. The final concentrations tested were 4, 8 and 16 µM, respectively. Control tubes were supplied with the same volume of sterile water in lieu of a phosphor dilution.

Each of final phosphor dilution (1:500, 1:1000 and 1:2000, respectively) was prepared in duplicate. The paired tubes were inoculated with two different concentrations of *Mycobacterium tuberculosis* culture: 1,000,000 cells/ml and 10,000 cells/ml. The same bacterial concentrations were inoculated into the phosphor-free control tubes. In addition, three non-inoculated tubes were set up with phosphor dilutions alone as a negative control. All of the higher inoculum tubes turned positive on day 5 of incubation (both with and without phosphor) and the low inoculum tubes became positive on day 7 (with and without phosphor). The non-inoculated control tubes remained sterile.

Accordingly, using the phosphor within the preferred concentration range does not affect growth of *M. tuberculosis* in the liquid culture medium tested. Comparable testing protocols, when used by one of skill in the art to test the toxicity of fluorescent pH indicators and color pH indicators, prove those markers also to be safe and effective for use in the present invention.

Example 2

A hollow form was assembled using two 3 inch by 4 inch (7.6 cm×10 cm) glass plates separated by 0.5 mm thick spacers to form a rectangular space. Agarose was added to a final concentration of 1% agarose (wt/vol) to liquid culture medium (pH 7.2) containing physiological saline, casein hydrolysate and glucose. The mixture was heated to near boiling for about 30 minutes to make the gelling culture medium. The gelling culture medium was allowed to cool to about 40° C., then phosphor and bovine serum albumin (BSA) was added. The phosphor, Oxyphor G2, a Pd-tetra (4-carboxyphenyl) tetrabenzoporphyrin dendrimer (Dunphy et al., *Anal. Biochem.* 310:191-198 (2002)), was added to a final concentration of 2 micromolar. The BSA, which was not sterilized, was added to a final concentration of 1% (wt/vol).

The phosphors useful in the instant invention generally are not heat labile. However, Oxyphor G2 requires BSA, which is heat labile, for binding to give the phosphor a quenching constant suitable for oxygen measurement in the instant invention. Thus, Oxyophor G2 and BSA were added after the gelled culture medium cooled down. Other phosphors suitable for use in the instant invention which, however, do not require the addition of BSA, and can be added to heated gelled culture medium or after it has cooled.

Approximately 3.8 ml of the gelling culture medium was injected into the hollow form using a hypodermic needle, and the form was filled by gravity flow. Because of the rapid gelling during this process, a few air bubbles formed. Warming the glass plates of the hollow form or filling the hollow form from a port at the bottom of the space are alternative, non-limiting ways to overcome the formation of air bubbles. Skilled artisans will know of methods to avoid air bubbles in gels.

The gel was incubated at room temperature, and phosphorescence intensity images were taken periodically to detect microorganism growth. A 450 nm LED was used to excite the oxygen-quenchable phosphor to phosphoresce, and the resulting phosphorescence was detected via a Xybion Gen 3 intensified camera (ITT Industries, Inc., San Diego, Calif.) equipped with a 695 nm long pass glass filter. The gelling culture medium was not deliberately inoculated with a microorganism. However, growing microorganisms were detected, most likely introduced with the non-sterile BSA. The identity of the detected microorganisms was not determined for this experiment.

Growth of the microorganisms was detected at 30 minutes (FIG. 3A). Note that the very dark regions rimmed with phosphorescence are the air bubbles that formed during pouring the gel. Additional colonies of growth were detected as the time of incubation progressed (FIG. 3B, 35 minutes incubation; FIG. 3C, 105 minutes of incubation and FIG. 3D, 120 minutes of incubation). At 105 minutes, numerous separate colonies were clearly detected as approximately circular areas of intense phosphorescence. An oxygen pressure map of the gel was also taken at 105 minutes using phosphorescence lifetime imaging with a frequency domain imaging phosphorimeter. As shown in FIG. 4, the dark spots are the localized regions of decreased oxygen pressure, detected by increased lifetime of the phosphor in the phosphorescence image, that result from the consumption of the oxygen by the growing microorganism.

Example 3

When the present detection/identification methods are applied to biological fluids, such as blood, that have low numbers of pathogens in a large volume of fluid, clinical requirements initially necessitate the use of large sample volumes. This could make the detection system large in size and cumbersome to work with, as well as difficult to construct and clean. Therefore, to meet this special need the sample holder is a hollow form as previously described having two flat glass or plastic plates separated by one or more spacers, and held together by suitable clamps or frame, or preformed as disclosed above. However, between the plates is inserted a simple, sterile, but disposable, puncture-resistant plastic bag ("culture bag"), into which the inoculated mixture is placed (the inoculated mixture as described above comprises the gelling culture medium in aqueous form prior to gelation with growth or metabolism indicator(s) and all necessary growth additives and gelling agent dissolved therein, and to which the test sample of microorganisms has been added).

The bag is then inflated with a sterile gas to exactly fit within the space between the plates. In the alternative, the bag is pre-inflated with a positive pressure of gas and then filled with the inoculated mixture, or the growth medium itself is used to inflate the bag. As a result, the hollow form holder requires little maintenance and only modest cleaning since it does not actually contact the medium. Therefore, is not likely to be contaminated or to contaminate subsequent cultures. Thus, the culture system does not require highly specialized care, is durable, and does not require replacement.

The disposable and inexpensive culture bags are prepared from thin plastic, which does not interfere with the optical measurements of growth in the contained culture medium containing agar or other gelling agent. The contained culture gels is removed from the hollow form in the bag, then if elected, the bag is cut or a press seal is opened and selected, identified cultured colonies are excised for further measurements or independent growth. A light sensitive dye added either on the bag or in the medium (e.g., attached to the gelling agent) and a laser marker or other marker permits the position of each colony of growing organisms to be marked to facilitate collection and/or staining of the cells in the colony.

While this particular growth chamber design and the use of plastic bags for the culture is primarily intended to facilitate use of the present technology with large sample volumes, it may also be adapted to any of the foregoing applications. In identifying microorganisms in a blood culture, where relatively large volumes are used to detect/identify the organisms that occur in very low numbers per ml of medium, a growth chamber with 0.5 cm spacing between 20 cm×20 cm plates produces a 200 ml culture volume, which is scalable either up or down. This system would be able to detect less than 1 organism/20 ml culture volume in a time only slightly longer than that if multiple smaller chambers were simultaneously prepared and used. However, by using the disposable plastic culture bags to contain the culture media, use of the system is simplified, making it much easier to use and far less expensive than any existing large volume culture method, and it permits much earlier detection of the microorganisms in the inoculated mixture. Thus, characterization of test microorganism(s) is facilitated, particularly in large volume/low microorganism count samples.

The disclosures of each patent, patent application and publication cited or described in this document are hereby incorporated herein by reference, in their entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

What is claimed is:

1. A method for rapidly detecting growth or metabolism of an immobilized cellular microorganism, the method comprising:
   placing a population of cells, comprising one or more microorganisms, into a sterile, liquid, aqueous, gelling culture medium, comprising a dissolved oxygen-quenchable phosphorescent compound that is non-toxic to the microorganism;
   evenly spacing and distributing the cells, without overlap, throughout the gelling medium;
   immobilizing the spaced and distributed cells by polymerizing the gelling medium, thereby forming a solid or semi-solid gel matrix $\leqq 3$ mm thick, immobilizing the cells therein;
   maintaining communicable contact between each cell and the oxygen-quenchable phosphorescent compound in the surrounding medium, such that the phosphorescent compound is responsive to oxygen pressure in the medium, while at the same time limiting exposure of the medium to only diffused external oxygen from the air into the gel, wherein non-uniform oxygen distributions form around each colony of growing cells;
   exciting the dissolved phosphorescent compound to phosphoresce; and
   detecting and measuring the phosphorescence in the gel matrix, wherein an increase in phosphorescence is indicative of growth or metabolism of the microorganism.

2. The method of claim 1, further comprising:
   inserting an inoculated mixture, comprising the liquid gelling medium together with the population of cells, into a space within a hollow-form growth chamber; and thereafter
   initiating formation of the gel, thereby immobilizing the cells contained therein within the growth chamber.

3. The method of claim 1, wherein the non-toxic, dissolved, oxygen-quenchable phosphorescent compound is a porphyrin compound having the formula:

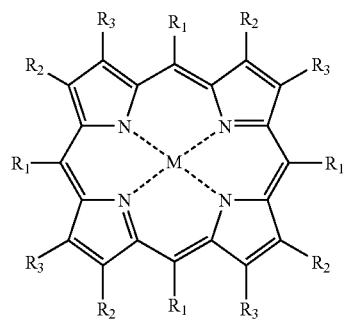

wherein: $R_1$ is a hydrogen atom or a substituted or unsubstituted aryl; $R_2$ and $R_3$ are independently hydrogen or are linked together to form a substituted or unsubstituted aryl; and M is $H_2$ or a metal.

4. The method of claim 3, wherein M is a metal selected from the group consisting of Zn, Al, Sn, Y, La, Lu, Pd, and Pt.

5. The method of claim 3, wherein the porphyrin is selected from the group consisting of porphyrin, tetrabenzoporphyrin, tetranaphthoporphyrin, tetraanthraporphyrin, and derivatives thereof.

6. The method of claim 5, wherein M is a metal selected from the group consisting of Zn, Al, Sn, Y, La, Lu, Pd, and Pt.

7. The method of claim 3, wherein the compound is a first, second, third, fourth or fifth generation dendrimer.

8. The method of claim 1, wherein the microorganism is selected from the group consisting of species from the genera *Bacillus, Mycobacterium, Actinomyces, Nocardia, Pseudomanas, Methanomonas, Protaminobacter, Methylococcus, Arthrobacter, Methylomonas, Brevibacterium, Acetobacter, Micrococcus, Rhodopseudomonas, Corynebacterium, Microbacterium, Achromobacter, Methylobacterium, Methylosinum, Methylocystis, Acinetobacter, Escherichia,* and mixtures thereof.

9. The method of claim 8, wherein the microorganism is further selected from the group consisting of the tuberculosis agents *Mycobacterium tuberculosis, M boris and M avium.*

10. A method for selecting and propagating at least one colony of one or more growing or metabolizing microorganisms, the method comprising:
    placing a population of cells, comprising one or more microorganisms, into a sterile, liquid, aqueous, gelling culture medium, comprising a dissolved oxygen-quenchable phosphorescent compound that is non-toxic to the microorganism;
    evenly spacing and distributing the cells, without overlap, throughout the gelling medium;
    immobilizing the spaced and distributed cells by polymerizing the gelling medium, thereby forming a solid or semi-solid gel matrix $\leq 3$ mm thick, immobilizing the cells therein;
    maintaining communicable contact between each cell and the oxygen-quenchable phosphorescent compound in the surrounding medium, such that the phosphorescent compound is responsive to oxygen pressure in the medium, while at the same time limiting exposure of the medium to only diffused external oxygen from the air into the gel, wherein non-uniform oxygen distributions form around each colony of growing cells;
    exciting the dissolved phosphorescent compound to phosphoresce;
    detecting and measuring the phosphorescence in the gel matrix, wherein an increase in phosphorescence is indicative of growth or metabolism of the microorganism;
    and selecting and removing from the gel at least one colony of the one or more microorganisms detected by an increase in phosphorescence indicative of growth or metabolism.

11. The method of claim 10, further comprising propagating the selected and removed colony in a separate sterile culture medium.

12. The method of claim 11, wherein the separate culture medium further comprises an antibiotic.

* * * * *